United States Patent
Makower

(10) Patent No.: US 8,075,580 B2
(45) Date of Patent: Dec. 13, 2011

(54) DEVICE, SYSTEM AND METHOD FOR INTERSTITIAL TRANSVASCULAR INTERVENTION

(75) Inventor: Joshua Makower, Los Altos, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 933 days.

(21) Appl. No.: 10/425,756

(22) Filed: Apr. 29, 2003

(65) Prior Publication Data

US 2004/0073238 A1    Apr. 15, 2004

(51) Int. Cl.
*A61M 29/02* (2006.01)
*A61B 18/12* (2006.01)

(52) U.S. Cl. .......................... 606/191; 606/40

(58) Field of Classification Search ............ 606/13, 606/14, 15, 16, 27, 28, 29, 32, 34, 37, 39–41, 606/45, 49, 52, 153, 169
See application file for complete search history.

(56) References Cited

U.S. PATENT DOCUMENTS

| | | | |
|---|---|---|---|
| 4,098,571 A | 7/1978 | Miyata et al. ................ 8/94.11 |
| 4,445,892 A | 5/1984 | Hussein et al. ............... 604/101 |
| 4,546,499 A | 10/1985 | Possis et al. ..................... 623/1 |
| 4,582,067 A | 4/1986 | Silverstein et al. ........... 128/663 |
| 4,633,870 A * | 1/1987 | Sauer ................................ 606/8 |
| 4,769,031 A | 9/1988 | McGough et al. ............... 623/1 |
| 4,808,153 A | 2/1989 | Parisi .............................. 604/22 |
| 4,924,863 A | 5/1990 | Sterzer ............................ 606/27 |
| 4,936,281 A | 6/1990 | Stasz ......................... 128/660.03 |
| 5,035,702 A | 7/1991 | Taheri ............................ 606/153 |
| 5,211,624 A * | 5/1993 | Cinberg et al. ................ 606/213 |
| 5,234,447 A | 8/1993 | Kaster et al. .................. 606/153 |
| 5,254,105 A | 10/1993 | Haaga ............................ 604/265 |
| 5,254,113 A * | 10/1993 | Wilk .................................. 606/8 |
| 5,269,297 A * | 12/1993 | Weng et al. ................... 606/128 |
| 5,287,861 A | 2/1994 | Wilk .............................. 128/898 |
| 5,364,389 A * | 11/1994 | Anderson .......................... 606/8 |
| 5,383,892 A | 1/1995 | Cardon et al. ................ 606/198 |
| 5,389,096 A | 2/1995 | Aita et al. ........................ 606/15 |
| 5,409,019 A | 4/1995 | Wilk .............................. 128/898 |
| 5,423,805 A | 6/1995 | Brucker et al. ................. 606/15 |
| 5,429,144 A | 7/1995 | Wilk .............................. 128/898 |
| 5,443,497 A | 8/1995 | Vendrux .......................... 623/1 |
| 5,452,733 A | 9/1995 | Sterman et al. ............... 128/898 |
| 5,470,320 A | 11/1995 | Tiefenbrun et al. ........... 604/174 |

(Continued)

FOREIGN PATENT DOCUMENTS

DE     4408746     9/1995

(Continued)

OTHER PUBLICATIONS

C. Massimo, L. Boffi; Myocardial Revascularization by a new method of carrying blood directly from the left ventricular cavity into the coronary circulation; J. Thoracic Surg. vol. 34 No. 2; Aug. 1957; pp. 257-264.

(Continued)

*Primary Examiner* — Ryan Severson

(57) ABSTRACT

Devices, systems and methods for transvascular interstitial interventions, including transvascular, catheter based vascular bypass, transmyocardial revascularization, bypass grafting of blood vessels, and interstitial surgical/interventional procedures wherein a catheter is advanced translumenally through the vasculature to a desired location and an operative instrument is passed through the wall of a blood vessel and to a target location (e.g. another blood vessel, an organ, a tumor, another anatomical structure) such that one or more operative devices may be advanced to the target location to perform the desired operative or interventional procedure.

2 Claims, 16 Drawing Sheets

U.S. PATENT DOCUMENTS

| | | | |
|---|---|---|---|
| 5,486,161 A | 1/1996 | Lax et al. | 604/22 |
| 5,531,677 A | 7/1996 | Lundquist et al. | 604/22 |
| 5,549,601 A | 8/1996 | McIntyre et al. | 606/15 |
| 5,556,377 A | 9/1996 | Rosen et al. | 604/22 |
| 5,591,226 A | 1/1997 | Trerotola et al. | 623/1 |
| 5,662,124 A | 9/1997 | Wilk | 128/898 |
| 5,676,670 A | 10/1997 | Kim | 606/108 |
| 5,695,504 A | 12/1997 | Gifford, III et al. | 606/153 |
| 5,702,412 A | 12/1997 | Popov et al. | 606/159 |
| 5,709,224 A | 1/1998 | Behl et al. | 128/898 |
| 5,725,544 A | 3/1998 | Rygaard | 606/167 |
| 5,749,375 A | 5/1998 | Maginot | 128/898 |
| 5,755,682 A | 5/1998 | Knudson et al. | 604/8 |
| 5,755,775 A | 5/1998 | Trerotola et al. | 623/1 |
| 5,758,663 A | 6/1998 | Wilk et al. | 128/898 |
| 5,766,163 A | 6/1998 | Mueller et al. | 606/7 |
| 5,797,920 A | 8/1998 | Kim | 606/108 |
| 5,797,934 A | 8/1998 | Rygaard | 606/153 |
| 5,800,540 A | 9/1998 | Chin | 623/11 |
| 5,827,268 A | 10/1998 | Laufer | 606/28 |

FOREIGN PATENT DOCUMENTS

| | | |
|---|---|---|
| EP | 347098 | 12/1989 |
| RU | 1822750 | 6/1993 |
| SU | 891076 | 12/1981 |
| WO | 9308738 | 5/1993 |
| WO | 9517131 | 6/1995 |
| WO | 9535065 | 12/1995 |
| WO | 9728745 | 8/1997 |
| WO | 9732532 | 9/1997 |
| WO | 9747261 | 12/1997 |
| WO | 9806356 | 2/1998 |
| WO | 9819625 | 5/1998 |

OTHER PUBLICATIONS

Martin Rossle, et al; The Transjugular intrahepatic portosystemic stent-shunt procedure for variceal bleeding; N. Engl J Med; vol. 330, No. 3; Jan. 20, 1994; pp. 165-171.

PS Goh, et al.; Transjugular intrahepatic portosystemic shunt: A case report; Singapore Med. J. vol. 34; 1993; pp. 453-455.

RK Grooters, et al.; Alternative Bypass Conduits and Methods for Surgical Coronary Revascularization; Chapter 21: the selective retrograde coronary venous bypass; 1994; pp. 209-215.

Ronald I. Weiner et al.; Development and Application of Transseptal Left Heart Catheterization; Catheterization and Cardiovascular Diagnosis vol. 15; 1998; pp. 112-120.

Jonathan Leor et al.; Iatrogenic coronary arteriovenous fistula following percutaneous coronary angioplasty; AHJ; Mar. 1992; pp. 784-786.

Christodoulos Stefanadis et al.; Autologous Vein Graft-Coated Stent for Treatment of Coronary Artery Disease; Catheterization and Cardiovascular Diagnosis vol. 38; 1996; pp. 159-170.

Wohl et al.; Report of the international working group on coronary sinus interventions; CSI—A new Approach to Interventional Cardiology; 1986; pp. 1-10.

Andrew Zalewski et al.; Myocardial protection via coronary sinus itnerventions: superior effects of arterialization compared with intermittent occlusion; Laboratory Investigation Myocardial Ischemia, vol. 71 No. 6; Jun. 1985; pp. 1215-1223.

Mark Hochberg et al.; Selective arterialization of the coronary venous system; J. Thoracic surg. vol. 77 No. 1; Jan. 1979; pp. 1-12.

Glen Rhodes et al.; Evaluation of regional myocardial nutrient perfusion following selective retrograde arterialization of the coronary vein; The Annals of Thoracic Surgery, vol. 25 No. 4; Apr. 1978; pp. 329-335.

Paul Yock et al.; Intravascular Ultrasound; Scientific Amercian Science & Medicine vol. 2, No. 5; 1995; pp. 68-77.

James Benedict et al.; Cardiac Vein Myocardial Revascularization; The Annals of Thoracic Surgery, vol. 20, No. 5; Nov. 1975; pp. 550-557.

Barry Kaplan et al.; Repair of a Coronary Pseudoaneurysm with Percutaneous Placement of a Saphenous Vein Allograft Attached to a Biliary Stent; Catheterization and Cardiovascular Diagnosis, vol. 37; 1996; pp. 208-212.

Russ Zajtchuk et al.; Revascularization of the Heart through the Coronary Veins; The Annals of Thoracic Surgery, vol. 21 No. 4; Apr. 1976; pp. 318-321.

Chiu et al.; Selective arterialization of coronary veins for diffuse coronary occlusion; J. Thoracic Surg.; Jul. 1975; pp. 177-182.

Arealis et al.; Arterialization of the coronary vein coming from an ischemic area; Chest, vol. 63, No. 3; Mar. 1973; pp. 462-463.

Grollman et al.; Percutaneous Embolic occlusion of an inadvertent surgical aortocoronary vein fistula; Catheterization and Cardiovascular Diagnosis, vol. 8; 1982; pp. 287-292.

Nakazaw et al.; Quantitation of anterior descending vs. circumflex venous drainage in the canine great cardiac vein and coronary sinus; Heart Circ. Physiol. vol. 3 No. 2; 1978; pp. H163-H166.

Nakamura et al.; Venous Flow in the Great Cardiac Vein of the Dog; Jpn. Heart J.; Jan. 1990; pp. 99-107.

Lopez et al.; Percutaneous Occlusion of an Iatrogenic Aortosaphenous Vein—Coronary Vein Fistula Via Retrograde Coronary Sinus Approach; Catheterization and Cardiovascular Diagnosis, vol. 37; 1996; 339-341.

Faxon et al.; Coronary Sinus Occlusion Pressure and Its Relation to Intracardiac Pressure; AJC vol. 56; Sep. 1985; pp. 457-460.

Pantely et al.; Effect of coronary sinus occlusion on coronary flow, resistance, and zero flow pressure during maximum vasodilatation in swine; Cardiovascular Research, vol. 22; 1988; pp. 79-86.

Robertson et al.; The Physiology, Pathology and clinical significance of experimental coronary sinus obstruction; Surgery, vol. 9 No. 1; Jan. 1941; pp. 1-24.

Beck et al.; Venous Stasis in the coronary circulation; AHJ;Jul. 1940; pp. 767-779.

Silver et al.; The functional anatomy of the human corona sinus; AHJ, May 1988; pp. 1080-1084.

M Von Ludinghausen; Clinical anatomy of cardiac veins, Vv. Cardiacae; surgical Radiologic Anatomy, vol. 9; 1987; pp. 159-168.

Kassab et al.; Morphometry of pig coronary venous system; The American Physiological Society; 1994; pp. H2100-H2113.

Christensen et al.; anatomic and Functional Studies of the Coronary Circulation in the Dog and Pig; Am. J. Vet. Res.; Jan. 1959; pp. 18-26.

Gregg et al.; Studies of the venous drainage of the heart; Aug. 1947; pp. 13-25.

Muers et al.; The reflex cardiovascular depression caused by occlusion of the coronary sinus in the dog; Physiol, vol. 221; 1972; pp. 259-282.

Gross et al.; Experimental attempts to increase the blood supply to the dog's heart by means of coronary sinus occlusion; The Journal of Experimental Medicine; Jul. 1936; pp. 91-108.

Gensini et al.; Anatomy of the coronary circulation in living man; Circulation, vol. XXXI; May 1965; pp. 778-784.

Joseph Wearn; The role of the thebesian vessels in the circulation of the heart; Sep. 1927; pp. 293-318.

Beack et al.; Revascularization of the heart; JAMA; May 1948; pp. 436-442.

* cited by examiner

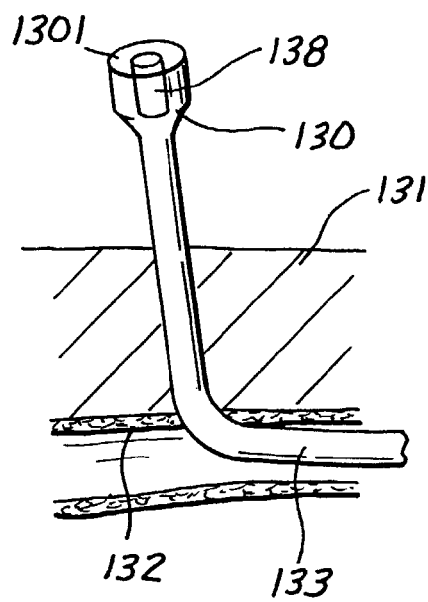
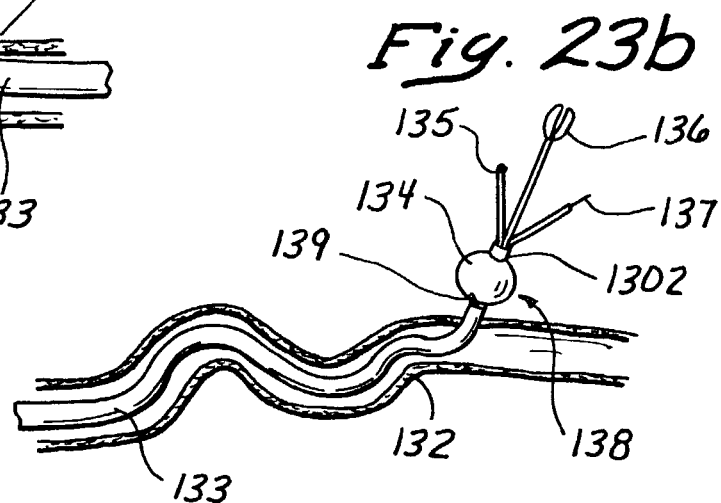
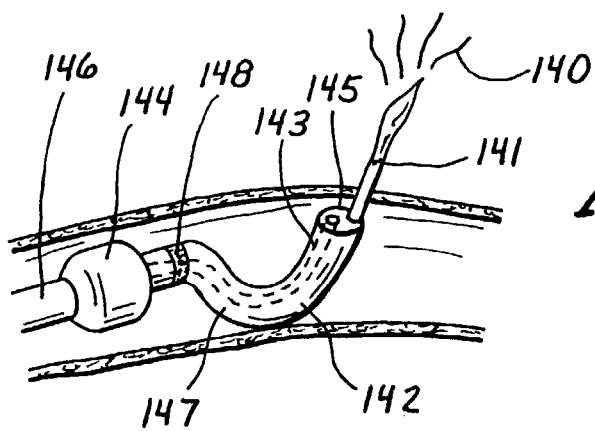
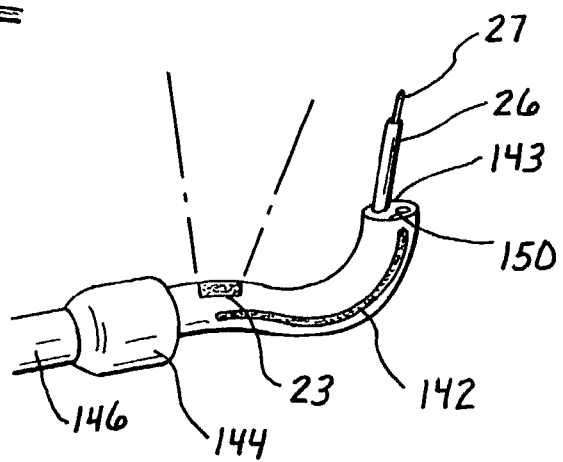

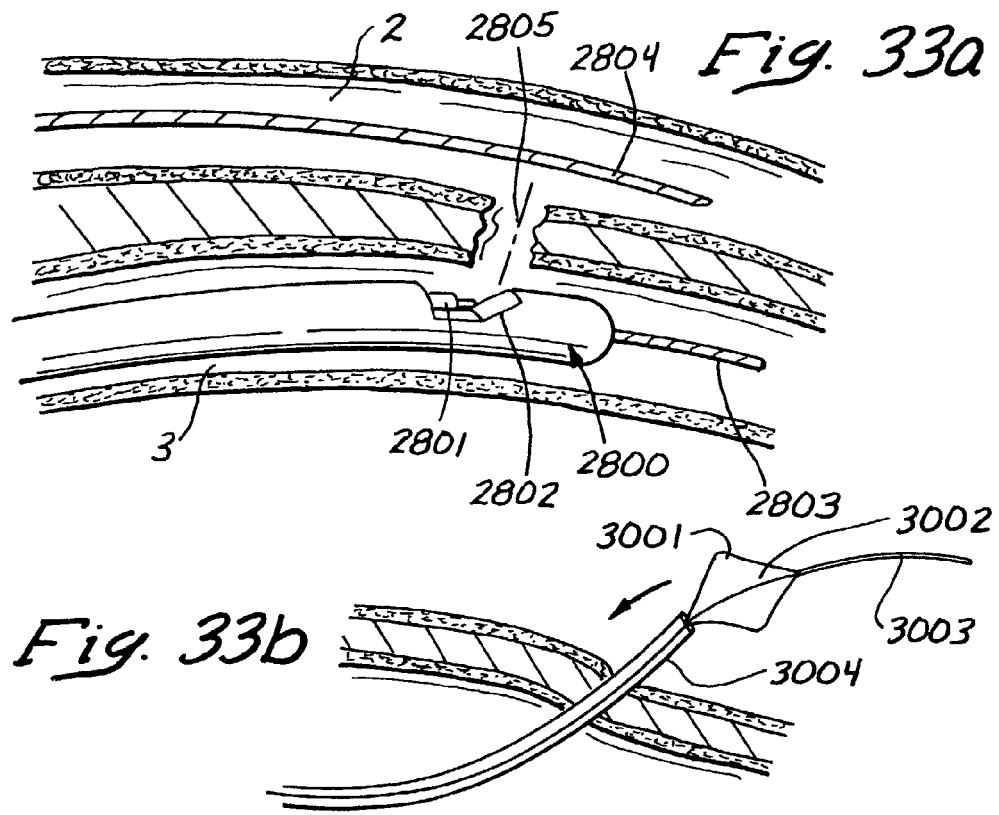
Fig. 33a
Fig. 33b
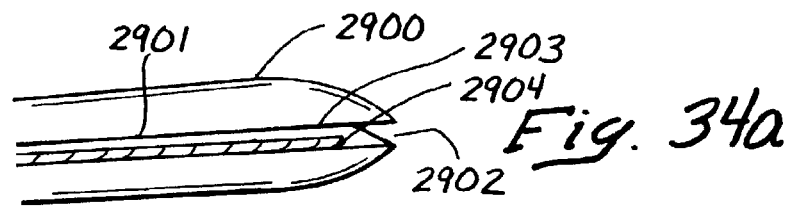
Fig. 34a
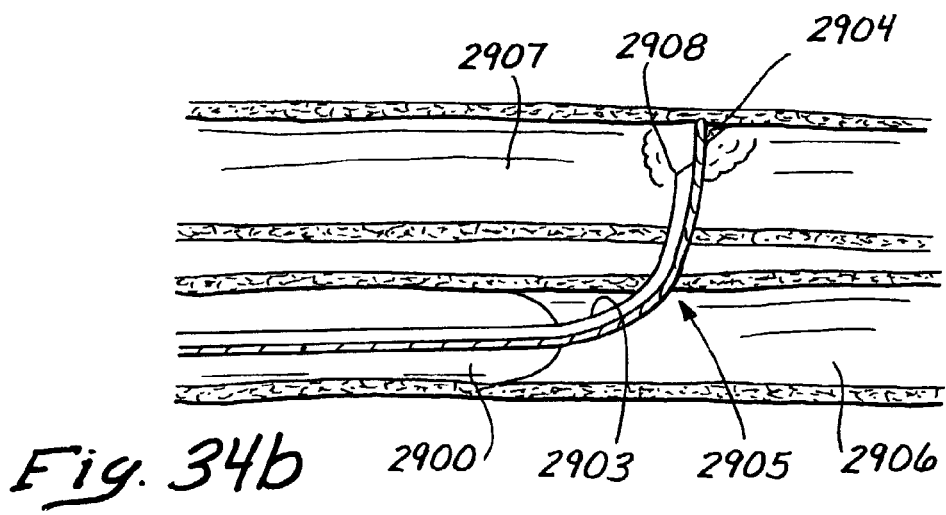
Fig. 34b

DEVICE, SYSTEM AND METHOD FOR INTERSTITIAL TRANSVASCULAR INTERVENTION

RELATED APPLICATIONS

This patent application is filed with a claim of priority to U.S. Provisional Patent Application Ser. No. 60/010,614 filed on Feb. 2, 1996, the entire disclosure of which is expressly incorporated herein by reference.

Also, filed contemporaneously herewith are three (3) separate applications entitled METHODS AND APPARATUS FOR BLOCKING FLOW THROUGH BLOOD VESSELS, METHODS AND APPARATUS FOR ANASTOMOSIS OF ANATOMICAL CONDUITS, and CATHETERS AND RELATED DEVICES FOR FORMING PASSAGEWAYS BETWEEN BLOOD VESSELS OR OTHER ANATOMICAL STRUCTURES, each of which includes subject matter which was initially included in U.S. Provisional Patent Application Ser. No. 60/010,614 and claims priority to that provisional application.

BACKGROUND OF THE INVENTION i. Percutaneous Transvascular Arterial Bypass

Atherosclerosis is a progressive disease process in which the flow within the lumen of an artery becomes restricted by a blockage, typically referred to as an atherosclerotic plaque. In the heart, as well as the periphery, a blockage of an artery can result in pain, disfunction and even death. Numerous methods have been employed over the years to revascularize the tissue downstream of an arterial blockage. These methods include bypass grafting using artificial, in-situ venous, or transplanted venous grafts, as well as angioplasty, atherectomy and most recently, laser transmyocardial revascularization. Bypass grafting has been extremely successful; however, the procedure requires extensive surgery. Recently, newer techniques such as the transthoracic endoscopic procedure being pursued by the companies, Heartport, Inc. and Cardiothoracic Systems, Inc., illustrate the need for a less invasive method of bypassing coronary vessels. These procedures are very difficult to perform, and may not be widely applicable. While transmyocardial laser revascularization, a technique in which small holes are drilled through the wall of the heart, looks promising, the method of action is not yet well understood, and problems exist with the use of laser energy to create the channels. Yet clinicians are still very interested in the technique because it has the potential to be minimally invasive, and does not require the patient to be placed on cardiopulmonary bypass.

In the 1970s several cardiovascular surgeons experimented with the use of cardiac veins for revascularization. The procedure was for use on patients which had severally diffuse stenotic coronary vessels. The technique involved using an intervening graft from the internal mammary artery or an aortic attachment to a saphenous vein. Instead of sewing the grafts to the distal coronary artery, the grafts were attached to the coronary or cardiac vein in the same location. The proximal portion of the vein was then ligated to prevent a shunt, and the patient was then taken off cardiopulmonary bypass, and the chest was closed. In this model, the veins were "arterialized", allowing flow in a retrograde fashion in an effort to bring oxygenated blood to the venules and capillaries of the heart. The success of this technique varied greatly, and was for the most part abandoned. Problems included stenosis at the anastomosis, intracardiac hemorrhages from ruptured venules, and thrombosis of the grafts.

The devices, systems and methods proposed in this disclosure suggest a new method of percutaneous revascularization. Here, the cardiac veins may either be arterialized, or may be simply used as bypass grafts. There is no literature to suggest that this has ever been attempted. While in-situ bypass grafts have been made in periphery, still an incision is made to attach and ligate the vein ends. Another procedure which bears some resemblance to this technique is called the TIPS procedure transjugular intrahepatic portosystemic shunt. In this procedure a stent is advanced into liver tissue to connect the portal vein to the inferior vena cava. While this procedure can be accomplished percutaneously, it is not for the purpose of revascularization of an organ or to bypass a blockage within a vessel, does not permit retrograde flow within either of the two vessels, is not performed with an accompanying embolization, and requires the use of a stent. Further, the devices and methods used in that setting are too large and do not have the directional capability necessary for use in smaller vessels such as those found in the heart.

ii. Transvascular Intervascular Interstitial Surgery

Open surgery was for many years the only way to gain access to tissues to perform a surgical maneuver. With the advent of optics, various endoscopic procedures were developed. Initially, these procedures utilized natural orifices such as the urinary tract, oral cavity, nasal canal and anus. Most recently, new techniques using transabdominal and transthoracic ports have been developed. These thorascopic or laporoscopic procedures essentially use instruments which are long shafted versions of their counterparts in open surgery. General anesthesia is usually required, and there are still several smaller wounds which require healing.

Another problem that exists with this approach is the identification of anatomically consistent reference points. For precise surgery, such as in the brain, a frame is usually attached to the patients head to provide this reference. More recently, a "frameless" system has been developed which utilizes a much smaller frame mounted with several light emitting diodes (LEDs). The LEDs are correlated to LEDs on the instrument itself using three cameras mounted to the ceiling. This aids in the correlation of the frame to the landmarks, and assures proper positioning of the instrument. While this seems like an extensive effort, it underlines the importance of gaining access to the exact location desired.

Traditionally, the vascular system has been entered for the sole purpose of addressing a vascular problem. Angioplasty, atherectomy, stents, laser angioplasty, thrombolysis and even intracardiac biopsy devices have all been designated for intravascular use.

iii. Intraluminal Closure

To date, there are several available schemes for closing off openings, vessels or tubular structures within the body involved in, for instance, the revascularization process. One method utilizes externally applied apparatuses such as staples, clips, sutures or devices which compress the opening externally and apply energy to weld them shut, for example, the Keppinger Forceps. While these methods are very successful, they all require access to the structure from the outside. However, this may not always be possible during certain catheter based inventions.

Another method, compatible with the catheter approach, involves the application of intraluminal devices such as detachable coils, balloons, injectable glues or emboli. These solutions are all limited by the requirement that a foreign object must be used to create a blockage. Moreover, the presences of a foreign object within the body, may at a later time, cause other problems. For example, these devices may become dislodged, or may cause a sever tissue reaction which can be of significant concern.

SUMMARY OF THE INVENTION

A device, system and method are provided for utilizing the vascular system as a conduit through which an intervention can be rendered within and beyond the vascular wall. In accordance with one embodiment, a device is introduced into the vascular system at a convenient entry point and is advanced to a particular target location at which point an opening is created to allow the passage of the device or another device or devices through or around the port into the space beyond the interior of the vessel. In one embodiment, a system is used to act as an access port to the space through which a procedure may be performed. Such a procedure may be worthwhile for cooling or ablating a volume of tissue, injecting or infusing a drug, substance or material, cutting, manipulating or retrieving tissue, providing access for endoscopic visualization or diagnosis, the placement of an implantable or temporary device, creating an alternative tract through which blood may be conducted for the purpose of revascularization or for performing some other surgical procedure. In another embodiment, the system is used to achieve an extraluminal percutaneous bypass. More particularly, the system is used to simultaneously achieve a second opening in an adjacent vessel proximate to the first opening so that an anastomosis channel may be created between the two vessels or conduits for the passage of blood therethrough. Such a procedure may be useful for creating alternative vascular channels to provide alternative revascularization routes, such as in the heart between the coronary arteries and cardiac veins, or in the periphery between adjacent veins, conduits and/or arteries. In one embodiment of the invention, the vessel with the second opening may be an in-situ vessel, a natural or artificial graft segment, or a transplanted vessel, all of which having been joined to the vessel with the first opening in a side-to-side manner. In other words, the two adjacent vessels, each having a substantially same size opening created by the system, may be maintained in approximation in a relatively parallel manner rather than the conventional end-to-side manner. With further specificity, such a system may be used to bypass coronary arteries and provide for cardiac venous arterialization, or segmental grafting. In addition, the stability of vascular supply orientation to anatomic landmarks provides a simple method of repeatedly accessing perivascular structures under imaging or other guidance. This may be particularly useful for accessing areas within the brain, kidney, lung, liver, spleen as well as in other tissues, and represents a significant advantage over tissue marking localization, external frames or so-called "frameless" external instrument orientation systems. In a further embodiment, the system is used to create an opening in the vessel proximally, tunneling through the tissue adjacent to the vessel, and re-entering the vessel at a distal point. This may be useful for providing an alternate path for blood flow around a lesion with a vessel. A final embodiment of the invention includes a system for closing off an opening such as a lumen of a vessel subsequent to the creation of an alternate revascularization route through which blood may flow around a diseased lesion. The system may use a suction mechanism to first pull the walls of the vessel so that the lumen may be temporarily closed. The system then provides means to securely fix the walls against one another to close off the lumen.

In accordance with one particular embodiment of the invention, there are provided methods and devices for transmyocardial revascularization, whereby transmyocardial passageways or bore holes are formed between one or more coronary blood vessels and one or more chambers of the heart, such that blood from the chamber(s) of the heart will flow through the transmyocardial passageways, thereby enhancing the perfusion of that region of the myocardium. In some instances, this may be accomplished by passing a passageway-forming catheter of the present invention through the coronary sinus and into a coronary vein. Thereafter, the passageway-forming catheter is utilized to form a plurality of transmyocardial passageways or bore holes from the coronary vein into a chamber of the left heart, preferably the left ventricle. Thereafter, the passageway-forming catheter is removed and the coronary vein is permitted to remain without occlusion, embolization or ligation, such that oxygenated blood from the left the left ventricle will flow freely through the transmyocardial passageways, through the coronary vein, and back into the coronary sinus. In this manner, a continual and unobstructed flow of arterial blood will be permitted to pass from the left ventricle, through the transmyocardial passageways, thereby providing for enhanced oxygenation and profusion of that region of the myocardium.

BRIEF DESCRIPTION OF THE DRAWINGS

FIG. 3b is a perspective view of the catheter shown in FIG. 3a, wherein the catheter has been rotated ninety degrees relative to the showing of FIG. 3a.

FIG. 12b is a side view of the apparatus of FIG. 12a.

FIG. 23a is a longitudinal sectional view of a blood vessel wherein a TVIS access port of the present invention has been percutaneously inserted.

FIG. 23b is a longitudinal sectional showing of a blood vessel having another embodiment of a TVIS access port of the present invention, which includes an optional balloon, inserted thereinto.

FIG. 24 is a longitudinal sectional showing of a blood vessel having a TVIS guide catheter of the present invention positioned therewithin, and a TVIS device (i.e., passageway forming catheter) advanced through such guide catheter.

FIG. 25 is a perspective view of another embodiment of a TVIS catheter of the present invention, having an active imaging component formed or mounted thereon.

FIG. 29d' is a longitudinal sectional view through the coronary vein shown in FIG. 29d.

FIG. 31b is a perspective showing of the locking guide wire apparatus shown in FIG. 31a.

FIG. 33a is a longitudinal perspective showing of adjacent blood vessels wherein an alternative TVIS catheter device of the present invention is being utilized to form a passageway or anastomosis channel between the blood vessels by emission of a vaporizing energy beam.

FIG. 33b is a longitudinal perspective showing of adjacent blood vessels having an initial puncture tract or passageway formed therebetween, and a device of the present invention passed therethrough for widening or enlargement of the initial puncture tract or channel.

FIG. 34a is a longitudinal sectional view of the distal tip of a TVIS catheter device of the present invention having a tissue-penetrating probe formed of shaped memory material retracted thereinto.

FIG. 34b is a longitudinal sectional showing of adjacent blood vessels having the TVIS catheter of FIG. 34a advanced thereto, and showing the shaped memory tissue-penetrating probe being advanced out of the distal end of the catheter to form an initial puncture tract or passageway between the blood vessels.

DETAILED DESCRIPTION OF THE PREFERRED EMBODIMENT

The invention herein utilizes the vascular system as a perfect conduit to any region of the body. The devices, system s and methods described herein provide a new way that the interstitial space can be accessed for surgical purposes. The invention described herein provides a system for gaining percutaneous access to any part of the body through the vascular system, and provides the basic set of instrumentation for accomplishing several surgical and medical end points.

The present invention provides a percutaneous means for revascularizing an organ fed by a diseased vessel. In accordance with further embodiments of the present invention, a complete multiple coronary artery bypass may be accomplished without cracking open the chest, general anesthesia or cardiopulmonary bypass.

In order to provide an overall understanding of the present invention, the method of the invention will be discussed with reference to the device's use to bypass a lesion within the coronary artery in the heart percutaneously. However, it will be understood by persons of ordinary skill in the art that the general method, system and device as described herein are equally applicable to the surgical manipulation of any perivascular structures. This invention represents a new concept in minimally invasive surgery which is that the vascular system may be used purely as a conduit to a desired surgical point. Under the proper guidance, at that surgical point, the perivascular space can be penetrated by a device so as to allow for the insertion of various instrumentation to create a surgical effect. Some examples of these procedures may include but are not limited to: transvascular intracranial access and subsequent therapeutic or diagnostic intervention to various perivascular tumors, hemorrhages, stroke affected areas and diseased zones; transvascular tissue biopsies from the brain, heart, kidney, liver, lung or bone; transvascular implantation of drugs, materials or devices such as sensors, radioactive seeds, ferromagnetic particles, balloons, cells or genetic material, and transvascular bypass.

Figure 1:
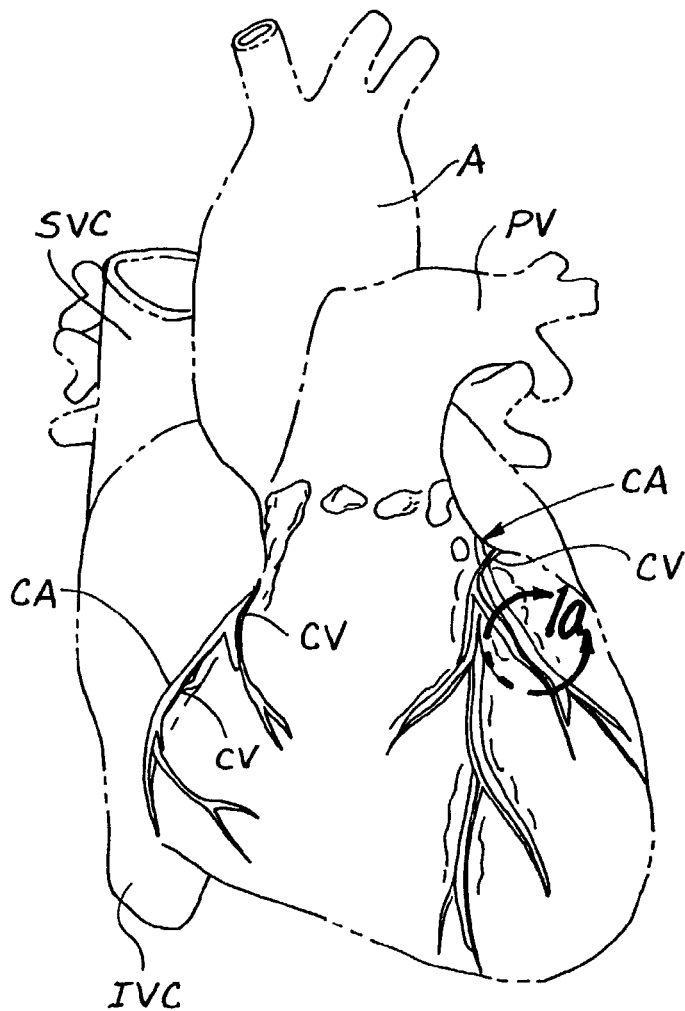
FIG. 1 is an anterior, perspective view of a human heart wherein catheters have been inserted to perform a translumenal coronary revascularization procedure wherein a segment of coronary vein is utilized as a bypass conduit for bypassing an obstruction in a coronary artery.
Figure 1A:
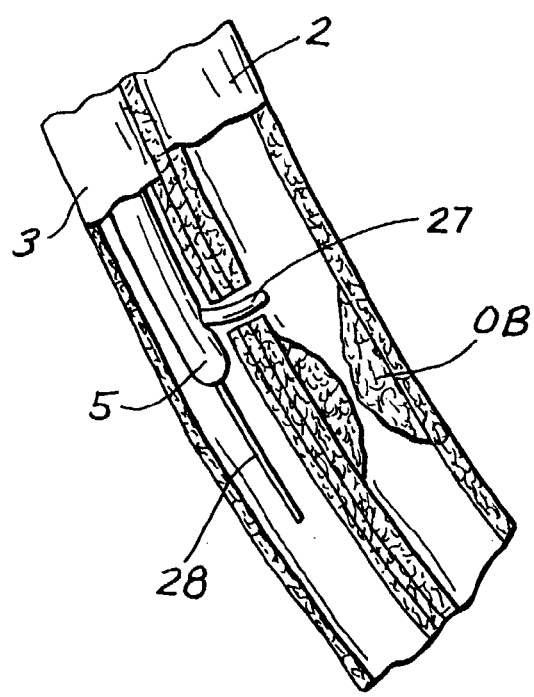
FIG. 1a is an enlarged, sectional view of the adjacent coronary artery and coronary vein within segment 1a of FIG. 1.

Referring to FIG. 1, a typical coronary sinus guide catheter 4 is shown having been advanced up the vena cava 7 and into the heart 1. Although not shown, the guide catheter 4 has been advanced into the coronary sinus within the right atrium of the heart 1. This guide catheter 4 will be of the type generally known in the art to include a tip of sufficient compliance and size to assure a traumatic insertion into the coronary sinus, with a balloon at its distal end to permit the retrograde injection of contrast to permit imaging of the cardiac venous system. The transvascular interstitial (TVIS) guide catheter 5 is inserted through the guide catheter 4 and advanced through one cardiac vein 3 over a guide wire 28 to a desired point adjacent to a coronary artery 2. The figure shows a TVIS probe 27 being advanced through the TVIS guide catheter 5 through an opening in the cardiac vein 3 to a desired point in the coronary artery 2.

Figure 2:
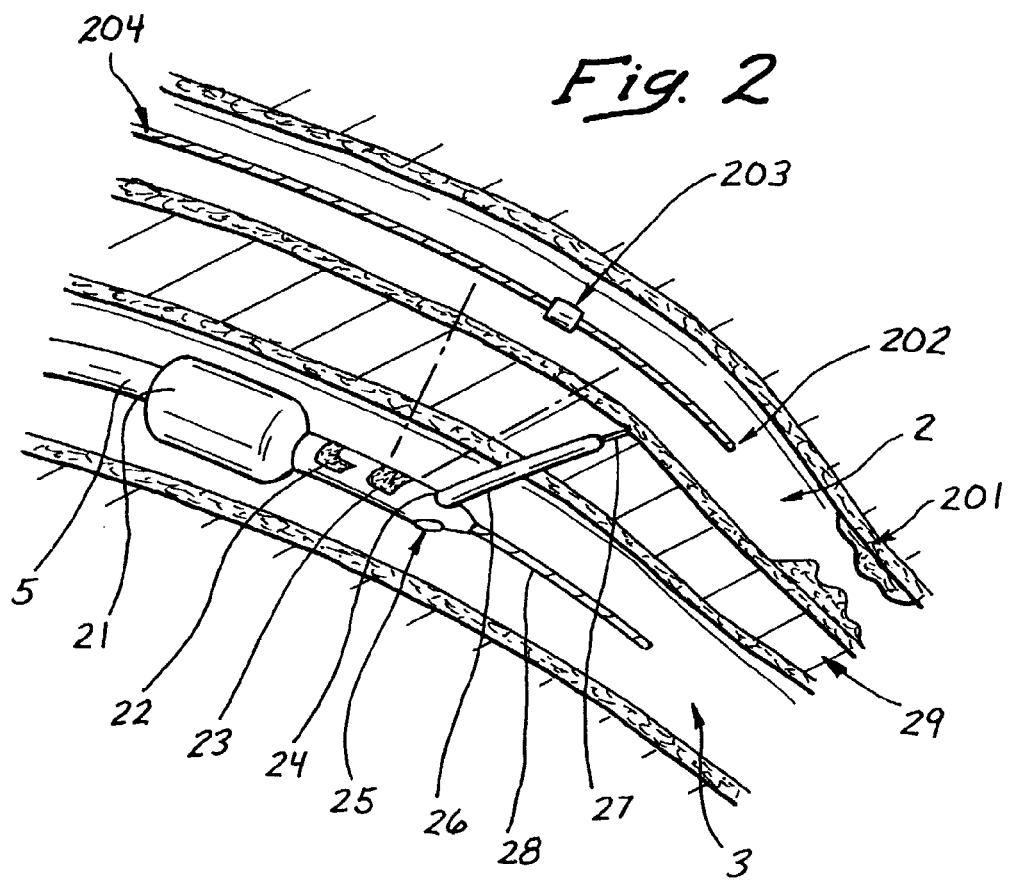
FIG. 2 is an enlarged, partial sectional view through a portion of the heart shown in FIG. 1.
Figure 3A:
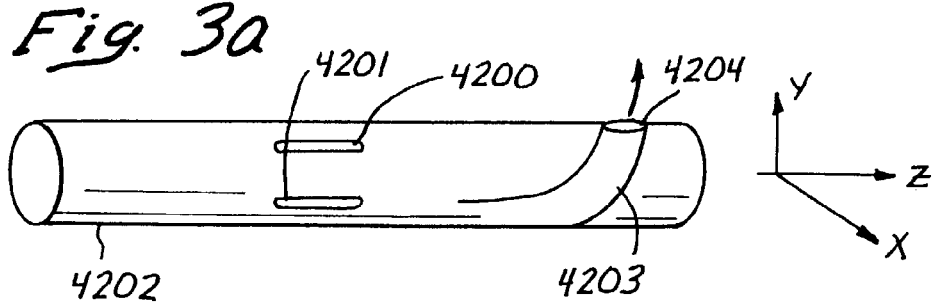
FIG. 3a is a perspective view of a passageway-forming catheter apparatus of the present invention having a first embodiment of an orientation marker system formed thereon.
Figure 3B:
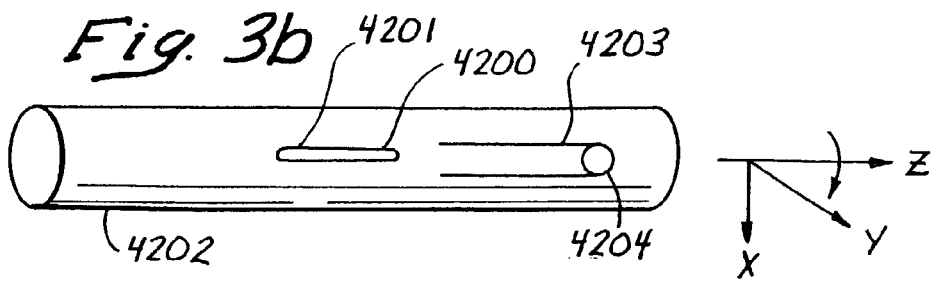
Figure 3C:
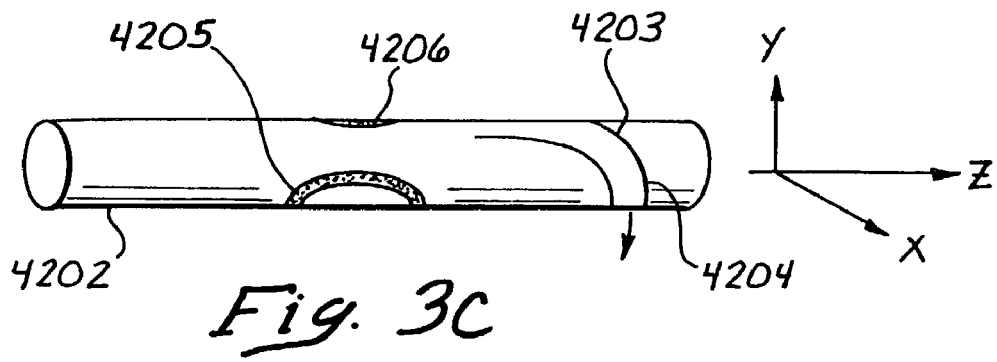
FIG. 3c is a perspective view of another passageway-forming catheter of the present invention having a second embodiment of an orientation marking scheme formed thereon.

FIG. 2 shows, in more detail, the various functions and components which could be included on the TVIS guide catheter 5. Here the TVIS guide catheter 5 is shown within a cardiac vein 3 being advanced over guide wire 28. A balloon 21 is provided on TVIS guide catheter 5 for the purpose of blocking flow, stabilizing the catheter within the lumen, or dilating the passageway. TVIS guide catheter 5 is also provided with either or both active orientation detection means 23 and passive orientation detection means 22. The passive orientation means 22 may be configured of any of a known set of materials which would allow for the radiographic, fluoroscopic, magnetic, sonographic or electromagnetic detection of the position and orientation of the distal portion of the TVIS guide catheter 5 within the body. These materials include but are not limited to any radiopaque material such as barium or steel, any ferromagnetic material such as those with iron, or any material or composite which provides sufficient interference to sound waves such as trapped air bubbles, scored metal or several laminates. The active orientation detection means 23 permits the proper 360 degree orientation of the distal portion on the TVIS guide catheter 5 within the lumen of the vessel, in this case cardiac vein 3. This active orientation means 23 can utilize any one but is not limited to one of the following technological schemes: the active orientation means 23 may be a simple piezoelectric, wire or silicon based slab capable of sending and receiving a signal to detect the presence or velocity of flow within an adjacent vessel; this same device could be an array of receivers in relation to a transmitter for the purposes of providing an image of the surrounding tissue; this same device could also be a simple transmitter capable of sending a signal to guide wire 202 positioned in this case within the coronary artery 2 where guide wire 202 is further modified to include a small receiver/transmitter 203 and wire bundle 204 capable of returning a signal to the operator upon detection of the signal emitted by active orientation means 23; the reverse system is also applicable where the small receiver/transmitter 203 sends a signal to active orientation means 23; the same could also be said for orientation means 23 to send or receive signals to or from any of a series of known signal generators including sonic, electromagnetic, light or radiation signals. The TVIS guide catheter 5 is provided in this case with an additional opening to allow for the selective injection of contrast or fluid into the vessel, in this case cardiac vein 3. Once the orientation of the TVIS guide catheter 5 is assured, the TVIS probe 27 and TVIS sheath 26 may be advanced through the wall of the cardiac vein 3 into the interstitial space 29 and into the coronary artery 2. The TVIS probe 27 and TVIS sheath 26 do not necessarily need to be advanced simultaneously and may have the following configurations: the TVIS sheath 26 may be a sharp tipped or semi rigid cannula capable of being inserted into the tissue alone; the TVIS probe 27 may be a relatively rigid wire, antenna, light guide or energy guide capable of being inserted into the tissue alone with the support of TVIS sheath 26; or further the TVIS probe 27 and TVIS sheath 26 may be operatively linked where the two are inserted together into the tissue. The TVIS probe 27 and/or the TVIS sheath 26 provide the initial connection between the two vessels, the cardiac vein 3 and coronary artery 2. In one embodiment of the invention, the TVIS sheath 26 may be made from stainless steel, nitinol or a polymer material. Once the TVIS sheath 26 is placed, a more floppy guide wire can be placed through it to permit the advancement of additional instrumentation in the case where another lumen is to be entered. Alternatively, no guide wire may be necessary if the interstitial space is being entered to perform a different type of procedure. This procedure may be used to create a bypass path from coronary artery 2 around a coronary stenosis 201, into the cardiac vein 3 and in some cases, back into the coronary artery 2. To further ensure accurate formation of a bypass path across two adjacent vessels, for example, a coronary artery to a cardiac vein, a catheter which has been inserted into one of the two vessels may be provided with a plurality of passive orientation detection means shown in FIG. 2 to correctly orient the direction of a TVIS probe. By way of example, each of the passive orientation detection means 4200 and 4201, as shown in FIG. 3a, may be situated on opposite sides of catheter 4202. In a preferred embodiment, detection means 4200 and 4201 are placed along a diameter across catheter 4202. In this manner, when the catheter 4202 is rotated about axis Z and the passive orientation detection means 4200 and 4201 subsequently become correspondingly aligned relative to one another, as seen in FIG. 3b, TVIS probe 4203 may be properly oriented within one vessel (not shown) so as to later form a bypass path across the adjacent vessels. Moreover, the passive orientation detection means 4200 and 4201 are positioned on catheter 4202 in such a manner that when viewed from the perspective of FIG. 3b (i.e., when the passive orientation detection means are in corresponding alignment with one another) they are in linear alignment with a distal portion 4204 of TVIS probe 4203 along axis Z.

Figure 3D:
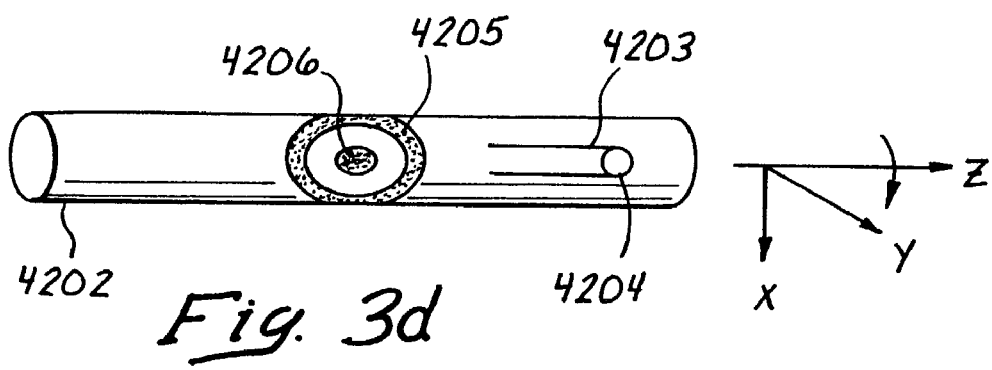
FIG. 3d is a perspective view of the catheter of FIG. 3c, wherein the catheter has been rotated ninety degrees relative to the showing of FIG. 3c.

In an alternate embodiment, the passive orientation detection means may be configured with a design as shown in FIGS. 42c and 42d. As illustrated, passive orientation detection means may comprise a substantially circular portion 4205 and a portion 4206 diametrically situated across catheter 4202. In other words, portion 4206 and the center of circular portion 4205 are situated along one diameter across the catheter 4202. To properly align the TVIS probe 4203 and its distal portion 4204 within a vessel for bypass path formation across to an adjacent vessel, catheter 4202 is rotated about the Z axis until portion 4206 and circular portion 4205 are concentrically aligned when viewed from the perspective of FIG. 3D.

Figure 3E:
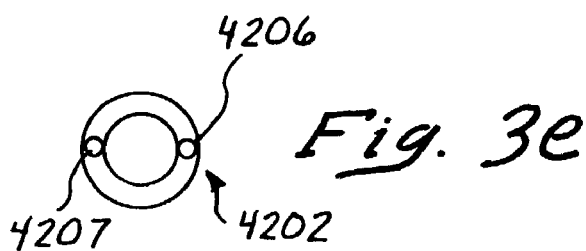
FIG. 3e is a cross sectional view through another catheter of the present invention having a third embodiment of an orientation marking system formed thereon.
Figure 3F:
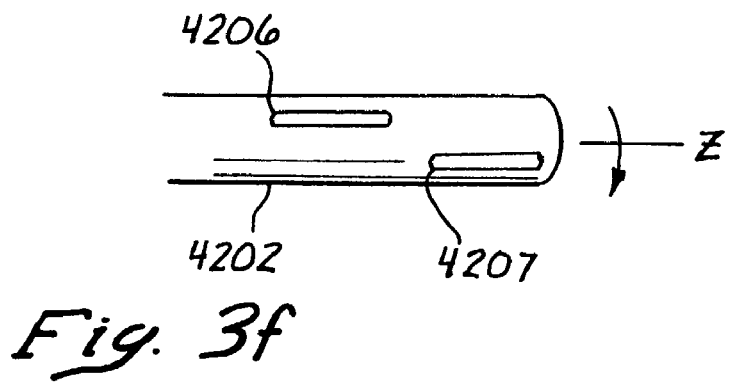
FIG. 3f is a partial perspective view of the catheter shown in FIG. 3e, wherein the catheter has been rotated approximately forty-five degrees relative to the showing of FIG. 3e.

In a further embodiment, the passive orientation detection means may be provided as shown in FIGS. 3e and 3f to include a plurality of segments, for instance, segments 4206 and 4207. When segments 4206 and 4207 are viewed from one end of catheter 4202, as illustrated in FIG. 3e, they are substantially parallel along a diameter of catheter 4202. However, when looking at catheter 4202 from a side view, as seen in FIG. 3f, segments 4206 and 4207 are not diametrically aligned as seen in FIGS. 3a and 3b. Rather, these segments are offset from one another such that when catheter 4202 is rotated about axis Z to properly orient the TVIS probe (not shown) within the vessel, segments 4206 and 4207, and the distal portion 4204 of the TVIS probe are essentially aligned in series.

Although only three different embodiments for the passive orientation detection means are shown, it should be appreciated that, for instance, other geometrical designs may be provided on the catheter such that when visualization of a particular geometry occurs, it may be said that a proper orientation of the TVIS probe has been achieved. Non-geometrical embodiments may also be provided so long as such an embodiment provides a proper orientation of the TVIS probe to form a bypass path from within one vessel to an adjacent vessel.

Figure 4:
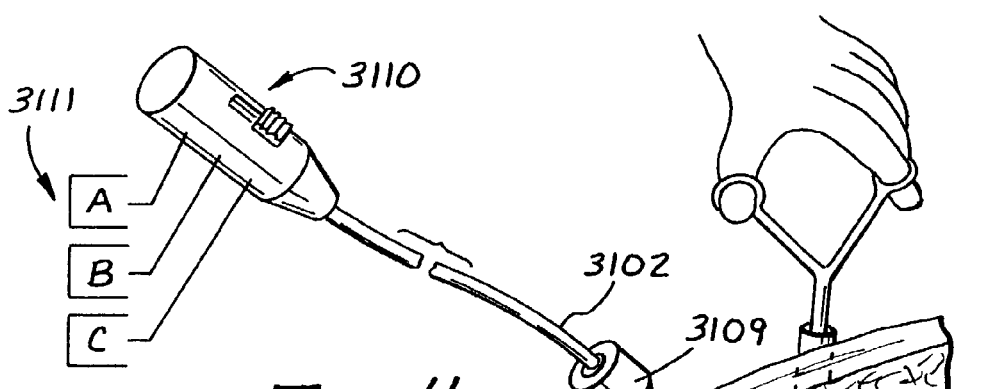
FIG. 4 is a perspective view of a procedure for attaching a bypass graft to a coronary artery, in accordance with the present invention.

In accordance with a further embodiment of the present invention, a bypass vessel, as illustrated in FIG. 4, may be attached to a coronary vessel with a stenosis in a side-to-side manner so as to provide an extraluminal percutaneous bypass path around the coronary stenosis. To understand the particular method, the discussion is provided with reference to devices for generally performing an extraluminal percutaneous bypass of a coronary vessel or an arterial vessel in the periphery using a graft segment, an in-situ vessel or a transplanted vessel.

FIG. 4 illustrates a procedure using an artificial or biological graft segment to bypass either a coronary vessel or an arterial vessel in the periphery. An artificial or biological graft segment 3101 may be positioned against a vessel 3106 within the body, and in this instance, in the heart 3107. Graft segment 3101 may be made from an artificial material such as PTFE or Dacron, or a biological material such as mammary artery, saphenous vein or other suitable tubular conduit. As shown in FIG. 4, a probe 3102 may be inserted through an entry point 3105 on graft segment 3101. Alternatively, probe 3102 may be inserted either within graft segment 3101 through one of its ends, or along side graft segment 3101 through a side branch. Purse stringed sutures 3104 are positioned about entry point 3105 to permit, upon completion of the procedure, rapid closure of the hole created by the entry point 3105. Probe 3102 is positioned about entry point 3105 to permit, upon completion of the procedure, rapid closure of the hole created by the entry point 3105. Probe 3102 is positioned within a body wall 3108 through port 3109 and has handle 3110 to permit control and modification of tip 3103. Handle 3110 may be connected to a range of external devices 3111 such as fluid irrigation/suction, radio frequency (RF) energy, ultrasound imaging hardware, doppler hardware, endoscopic imaging apparatuses, other energy sources such as microwaves or lasers, and mechanical actuation means. The purpose of probe 3102 is to provide mechanical support and, if necessary, to detect the proper location for the graft to be placed. A grasper 3112 is also shown in FIG. 4 assisting in the placement and stabilization of the graft segment 3101. Once positioned correctly, stay sutures or an attachment agent 3113 such as a surgical adhesive may be used to hold the graft in place against the vessel 3106 during subsequent maneuvers. Although the procedure is discussed in connection with the heart, it should be appreciated that the procedure is equally applicable to arterial vessels in the periphery.

Figure 5:
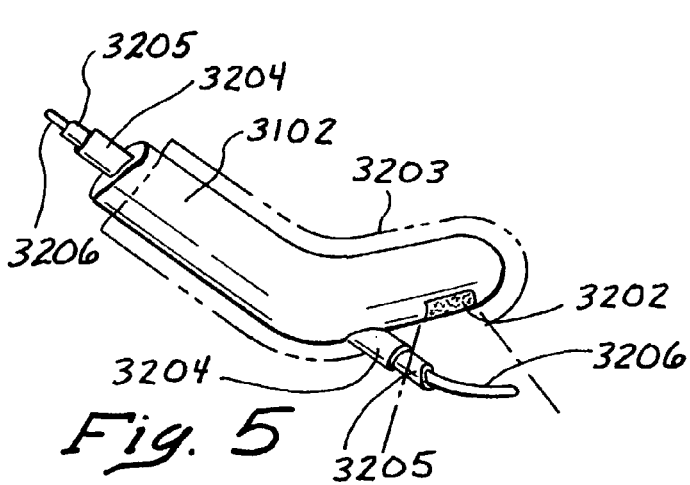
FIG. 5 is an enlarged view of the distal portion of a passageway-forming probe apparatus utilized to form a passageway and connection between the graft and the coronary artery in the procedure shown in FIG. 4.

FIG. 5 illustrates, in detail, the tip of the probe 3102 shown in FIG. 4. Here a probe shaft is shown terminating in a probe tip 3201. In one embodiment of the invention, angle 3208, at which the tip 3201 is positioned relative to the shaft 3207, may be variable. Alternatively, the relative angle between the tip 3201 and the shaft 3207 may be fixed. On the tip 3201, detection means 3202 is positioned in or next to (as shown) access means 3205. The detection means 3202 provides information about the correct positioning of access means 3205 and may be a doppler imager or detector, ultrasonic imager or detector, or other detection means capable of sensing the presence of the desired vascular structure, for instance, a vessel. In cases where the vessel is clearly visible, such a detection scheme may not be necessary. Nevertheless, access means 3205 may be provided with a number of configurations. The configuration shown in FIG. 5 allows for a flexible sheath 3204 to be introduced over the access means, and for a guide wire 3206 to be introduced percutaneously from within. Alternatively, a sharp wire could be used to access the vessel with a flexible sheath over it, permitting the sharp wire to be subsequently exchanged for a more a traumatic guide wire. FIG. 5 further shows graft 3203 in outline around a probe shaft 3207 and tip 3201. Graft 3203, as previously indicated, may be an artificial or biological graft segment (or transplanted vessel from a nearby area). Once the probe within the graft 3203 is properly positioned adjacently to a vessel with a stenosis, access means 3205 is used to puncture simultaneously through both the walls of the graft 3203 and the adjacent vessel similar size openings so as to create a channel therebetween. The presence of such an anastomosis channel is preferable as it permits a guide wire to be introduced between the graft and the vessel so that the sizing of the channel and the attachment of the graft to the vessel may subsequently be carried out across the channel. It should be appreciated that any artificial or biological graft segment (or transplanted vessel from a nearby area) may be positioned over or along side such structures as the femoral or popliteal arteries or veins, the coronary arteries or veins, the aorta, the carotid or iliac arteries, the vena cava, or any other tubular structure within the body to perform the indicated bypass.

Figure 6:
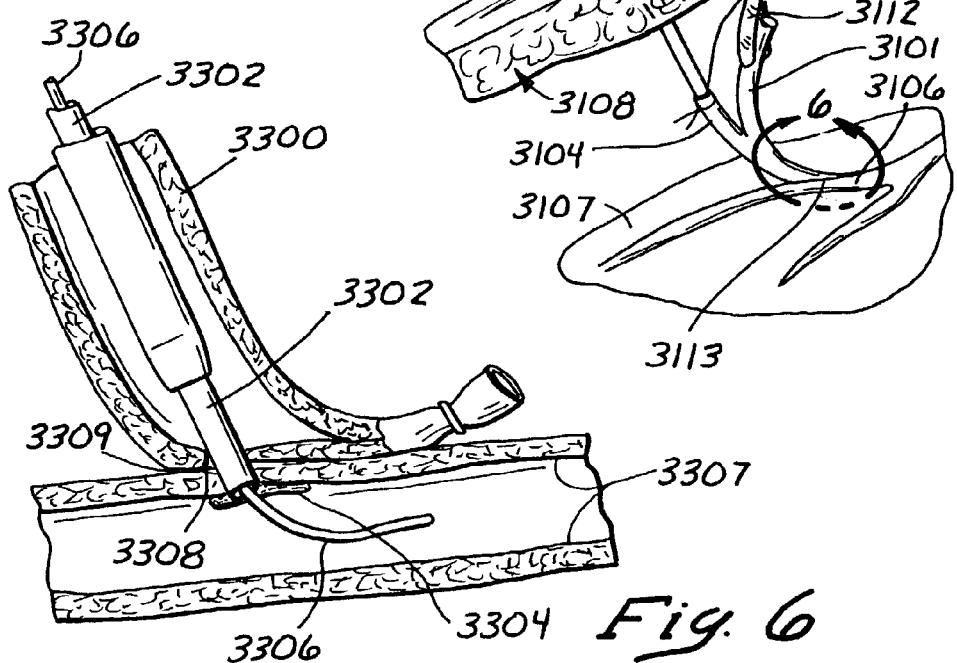
FIG. 6 is an enlarged cut away perspective view of segment 6 of FIG. 4.

FIG. 6 shows, in accordance with a preferred embodiment of the invention, a procedure for joining, across an anastomosis channel 3305, two vessels in a side-to-side manner for bypassing a stenosis. Graft 3300, which may be an artificial or biological segment, or a transplanted vessel from a nearby area, may be positioned against vessel 3307 using probe 3301, and the scheme described in FIGS. 4 and 5. Graft 3300 may subsequently be affixed in place with an attachment means, for instance, a surgical adhesive 3309. The attachment means, for example, stay sutures, energy based welding, glues, or magnetism may be used to hold the two vessels in apposition. Since an artificial or biological segment, or a transplanted vessel from a nearby area is used as a bypass conduit in a side-to-side procedure discussed herein, one or both ends of graft 3300 may be terminated with a clip 3303 to prevent leakage of flow therefrom. Over a guide wire 3306, an attachment delivery device 3302 is introduced to junction 3308 between the graft 3300 and the vessel 3307 to deploy an attachment member thereat. One type of attachment member useable for this purpose is an anastomosis stent 3304 having a clover shape, a complete description of which is set forth in co-pending U.S. patent application Ser. No. 08/730,327 filed on Oct. 11, 1996, now U.S. Pat. No. 6,190,353 and claiming priority to earlier filed Provisional Application Ser. No. 60/005,164. Alternatively, other channel connector devices may be used, such as those described in PCT International Patent Application No. PCT/US97/01968 entitled METHODS AND APPARATUS FOR CONNECTING OPENINGS FORMED IN ADJACENT BLOOD VESSELS OR OTHER ANATOMICAL STRUCTURES, which is being filed contemporaneously with this application.

Figure 6A:
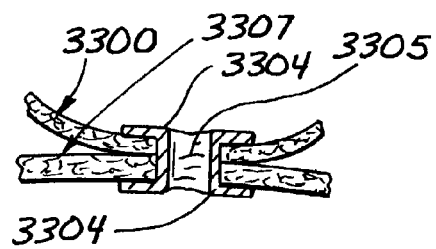
FIG. 6a is an enlarged view of the passageway and connection formed between the graft and the coronary artery in the procedure of FIG. 4.

As illustrated in FIG. 6a, the anastomosis stent 3304 or other channel connector device is used to provide an extraliminal connection between the lumen of vessel 3307 and the lumen of graft 3300. In addition, stent 3304 is used to hold the vessel 3307 and the graft 3300 in close approximation and to maintain the size of the anastomosis channel 3305. However, it should be appreciated that the attachment member (i.e., anastomosis stent) for maintaining the size of the anastomosis channel may be any number of devices, for instance, a stapler, an internal clipper, a stent, or a welder.

Figure 7:
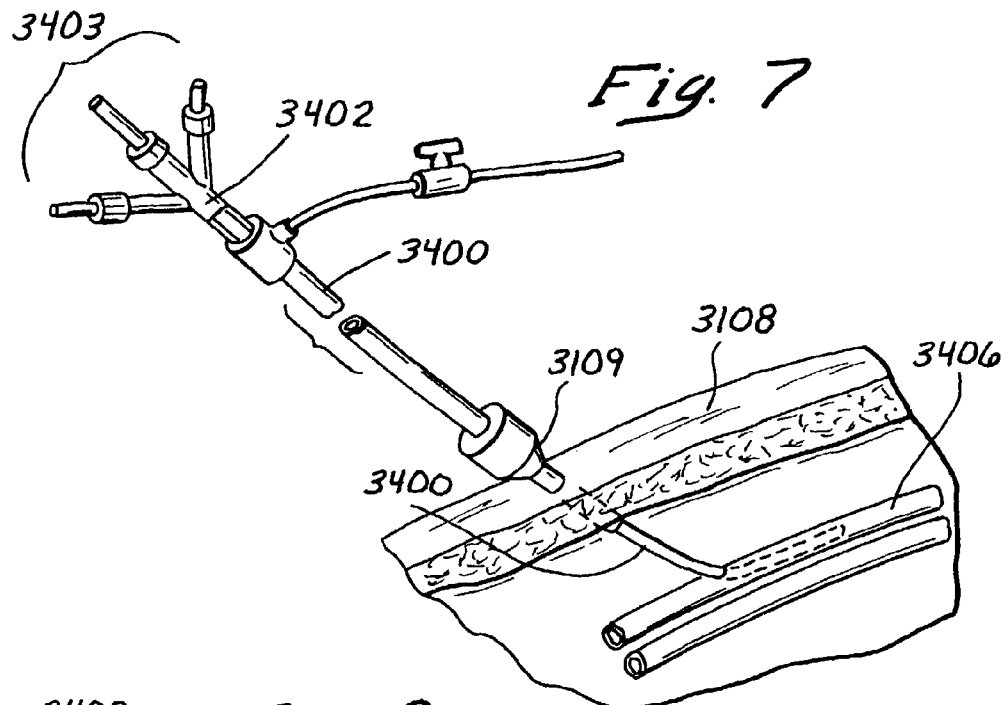
FIG. 7 is a perspective view of a portion of the human thorax showing a method for performing a minimally invasive in situ bypass procedure to bypass an obstruction in a coronary or peripheral blood vessel.
Figure 8:
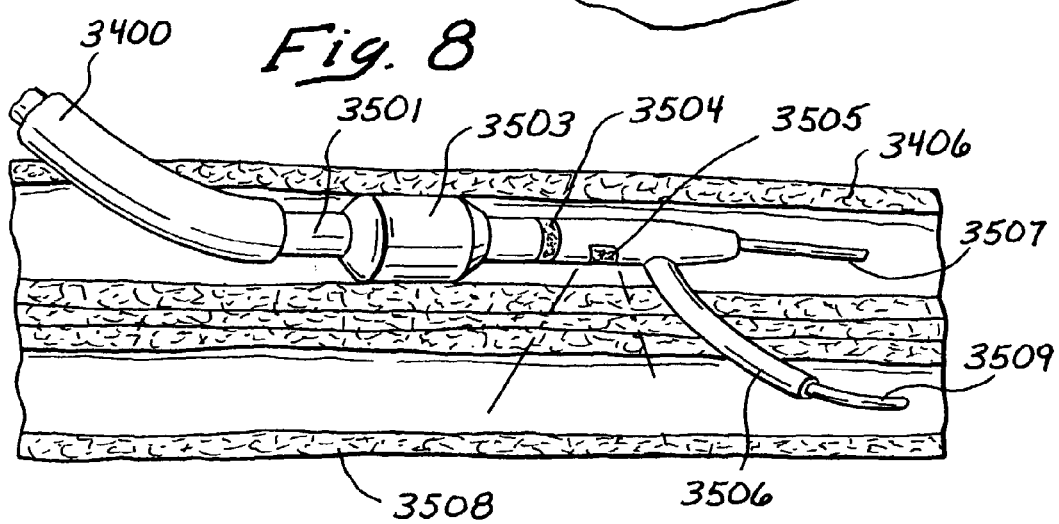
FIG. 8 is a perspective cut away view of an adjacent artery and vein having an introducer and access catheter of the present invention inserted thereinto for use in performing an in situ bypass procedure whereby blood from one of the blood vessels is caused to flow into the lumen of the other blood vessel.

FIGS. 7 and 8 illustrate an in situ bypass procedure for a coronary vessel or an arterial vessel in the periphery. In an in situ bypass procedure, vessels 3405 and 3406, one of which is to be bypassed, naturally lie in close proximity to one another, rather than having been brought into that position. Introducer 3400, as shown in FIG. 7, is initially inserted through port 3109, across the body wall 3108, and into one of the two adjacent vessels 3405 and 3406. An access catheter 3401 is thereafter introduced through introducer 3400 and manipulated so that its tip 3404 is threaded into a proper position within one of the vessels, for example, vessel 3406. In one embodiment of the invention, access catheter 3401 includes a hub 3402 having a plurality of access ports 3403 so as to permit the introduction or removal of, for example, various devices, energy delivery means, or fluids and gasses.

FIG. 8 illustrates, in further detail, the introducer 3400 and access catheter 3501 within vessel 3502 which is to be bypassed. Access catheter 3501, similar to catheter 5 of FIG. 2, is shown having an optional balloon 3503, passive detection means 3504, active detection means 3505, sheath 3506 and guide wires 3507 and 3509. In this diagram, the guide wire 3509 has been substituted for a TVIS access probe 27 shown in FIG. 2. The in-situ bypass procedure discussed in connection herewith, is substantially similar to the procedure set forth in connection with FIGS. 4 and 5. In particular, the initial access within a vessel is accomplished endoscopically. Moreover, the isolation of an adjacently parallel vessel, and the percutaneous procedures for creating an anastomosis connection, and for attaching the vessels are conducted in very much the same way. The essential difference is that in an in-situ situation, a naturally adjacent vessel is used as a bypass conduit rather than an artificial or biological bypass segment. In addition, with an in situ procedure, the use of the active detection means to locate the bypassing vessel may be much more critical, especially if the endoscopic suite is not equipped with fluoroscopy.

Figure 9:
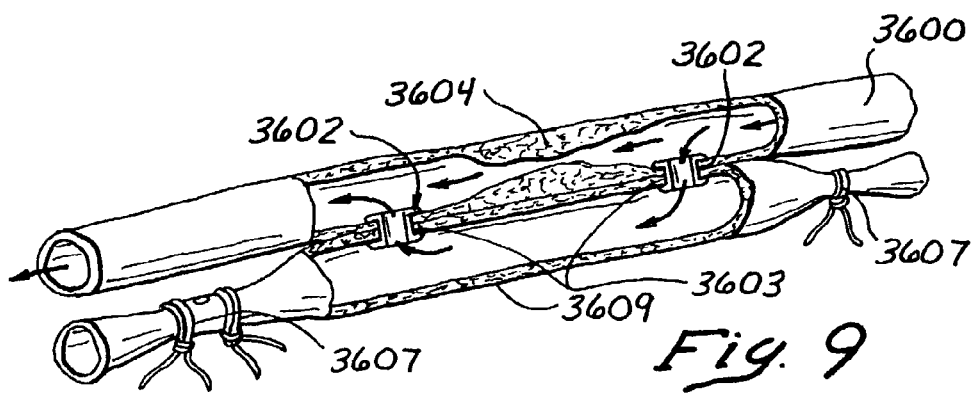
FIG. 9 is a cut away perspective showing of the final result of either an in situ bypass or bypass grafting procedure, in accordance with the present invention.

FIG. 9 illustrates an end result of a side-to-side procedure for either an in situ bypass or a bypass with a grafting segment. In such a procedure, since endoscopic access is readily available, the need for intraluminal blockage to prevent shunting may not be limited to the use of devices similar to an embolization apparatus (a discussion of which is provided hereinafter). Instead, both ends of vessel 3609 may be closed off using parallel sutures 3607 as shown. The parallel sutures 3607 may also be used to isolate a portion of vessel 3609 within which a hole. 3608 exists where the introducer had previously been placed. As previously indicated, the introducer may alternatively be placed directly into the end of the graft 3609, rather than through side hole 3608, in the event an artificial or biological graft segment is being used in the bypass procedure. As shown in FIG. 9, by joining a bypass vessel 3609 in a side-to-side manner to vessel 3600 which has a diseased lesion 3604, a small tissue track, such as anastomosis channels 3602 may be created using, for example, a dilating balloon, dissection and exposure, or endoscopic attachment as described earlier. The creation of anastomosis channel 3602 allows for fluid to flow into the bypassing vessel 3609 from vessel 3600 at a proximal location bypassing the lesion 3604. If it is desirable, another anastomosis channel 3602 may be created downstream of lesion 3604 so that fluid may flow around the lesion 3604, and back into vessel 3600 at a distal location. An anastomosis device 3603 may be used to maintain the channel 3602 and to maintain the two vessels in approximation. The vessels may also be maintained in approximation by other attachment means indicated above, or by welding the vessels against one another.

Figure 10:
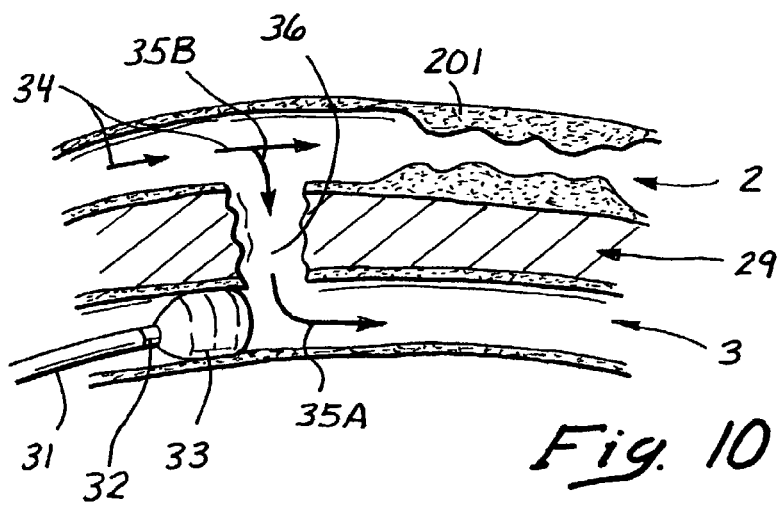
FIG. 10 is a longitudinal sectional view of two adjacent blood vessels having a blood flow passageway formed therebetween in accordance with the present invention, and a lumen blocking apparatus disposed within the lumen of the bypass vessel to facilitate the flow of shunted blood in the desired direction through the bypass vessel.

To prevent fluid such as coronary blood from shunting directly back through the bypassing vessel after the percutaneous creation of the anastomosis channel for bypassing the stenosis, it may be necessary to block flow at one or more points within the bypassing vessel. With reference now being made to a coronary bypass in FIG. 10, once a hole is made within cardiac vein 3, and it is determined that it is of sufficient size, an embolization device, such as an embolization balloon 33, can be used to block flow in the cardiac vein 3 in a region proximal to anastomosis channel 36. This maneuver ensures that coronary arterial flow 34 passes through anastomosis channel 36 and results in a retrograde cardiac venous flow indicated by arrows 35a and 35b. The embolization balloon 33 is placed using embolization catheter 31 and upon proper inflation, is detached via a detachable segment 32. Any one of several devices and materials are available for the purpose of embolization. These include detachable balloons, coils, strands of coagulation producing material, microfibrillar collagen, collagen sponge, cellulose gel or sponge such as Gelfoam, or special stents. FIG. 10 shows how these devices can be used to re-arterialize the venous system distal to the connection. However, as shown in FIG. 12, it is possible to simply provide a bypass path by performing the same procedure in reverse in an appropriate downstream location. It should be mentioned that these embolization devices may also be used to block off any unwanted tributaries branching off from the cardiac vein. FIGS. 4 and 9 are described later in this document.

FIGS. 11a-11b and 12a-12b depict two additional schemes of embolization device in accordance with the invention which also may have utility to accomplish the desired closure. These embolization devices, as well as others, are described in more detail in PCT International Patent Application No. [ ] PCT/US97/01463 entitled METHODS AND APPARATUS FOR BLOCKING FLOW THROUGH BLOOD VESSELS, which is being filed contemporaneously with this application.

Figure 11A:
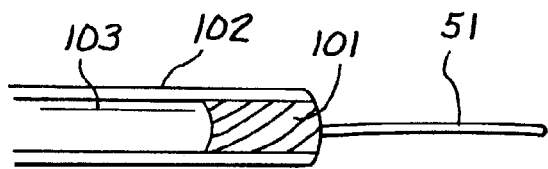
FIG. 11a is a longitudinal sectional showing of a delivery catheter having a self expanding embolization device in the nature of a gel foam sponge positioned within the lumen of the catheter, and advanced over a prepositioned guide wire.
Figure 11B:
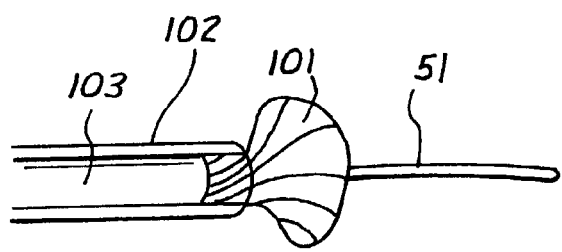
FIG. 11b shows the catheter of FIG. 11a wherein the self expanding embolization device in the nature of a gel foam sponge is being advanced out of the distal end of the catheter and over the guide wire.

The embolization device shown in FIG. 11a is a compressed collagen sponge 101 located within an outer sheath 102, capable of being delivered over guide wire 51. Once the guide wire 51 is advanced into vessel which is to embolized, outer sheath 102 is withdrawn over inner core 103 to permit collagen sponge 101 to expand into the vessel as seen in FIG. 11b. Once completely delivered, the guide wire 51 and the catheter assembly 102 and 103 are withdrawn, leaving the sponge in place.

Figure 12A:
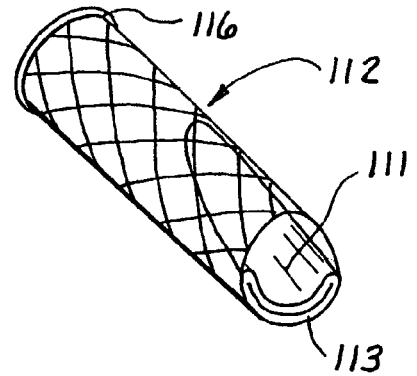
FIG. 12a is a perspective view of a one way valved stent apparatus which is usable to facilitate one way flow through the passageways formed between blood vessels or other anatomical structures, in accordance with the methods of the present invention.
Figure 12B:
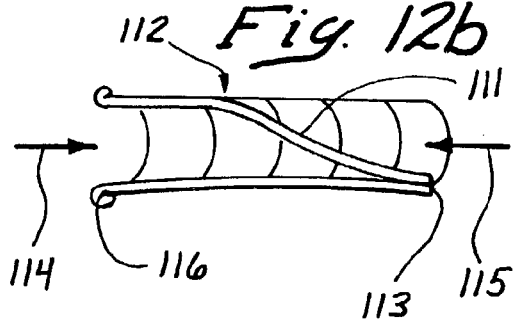

FIGS. 12a and 12b depict a one way valved stent 112. Membrane 111, disposed within the stent 112, is configured to be cylindrical at side 116, yet collapsed upon itself at side 113 to form a one way valve. As seen in longitudinal section FIG. 12b, this allows flow in the direction of arrow 114 and the advancement of devices in this direction, but prevents flow in the direction of arrow 115 as well as preventing devices from entering from that direction. The one way valve stent 112 can be easily placed over a catheter into the desired location and expanded to fit in position. Once the internal delivery catheters are removed, membrane 111 is allowed to collapse, instantly creating a valve like action.

Figure 15:
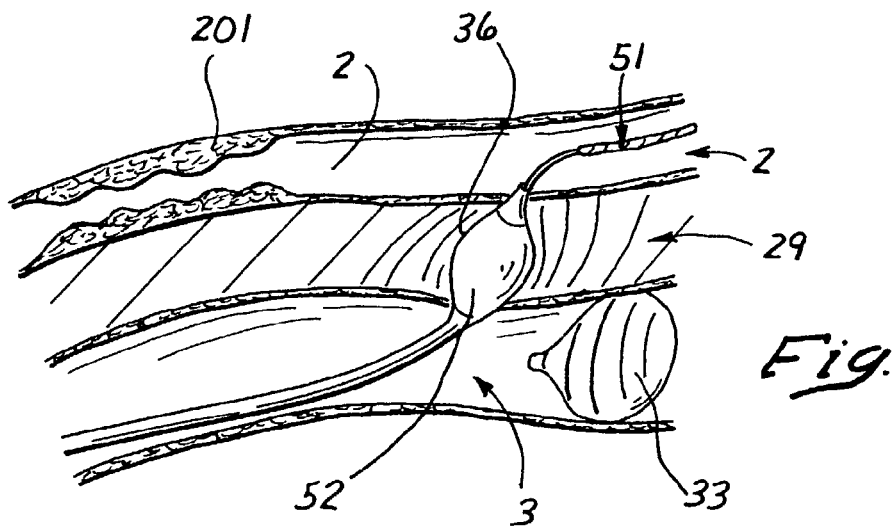
FIG. 15 is a longitudinal sectional view of adjacent blood vessels having a blood flow passageway or an anastomosis channel formed therebetween in accordance with the present invention, such blood flow passageway or anastomosis channel being dilated by a balloon which has been advanced over a guide wire for the purpose of dilating the passageway or an anastomosis channel.

It will be appreciated that the use of the collagen sponge 101 as shown in FIGS. 11a and 11b, or flow blocking or partially flow blocking stents 112 as shown in FIGS. 12a and 12b, are not the only means by which the normal flow of blood through the bypass vessel may be blocked. Indeed, certain energy emitting devices and systems useable for intraluminal welding or sealing of the vessel lumen (which were originally shown in FIGS. 37-40 of Provisional Application Ser. No. 60/010,614 to which this application claims priority) as well as other embolizers or lumen blocking apparatus, are now described and claimed in copending application No. PCT/US97/01463 entitled METHODS AND APPARATUS FOR BLOCKING FLOW THROUGH BLOOD VESSELS, which is being filed contemporaneously with this application, also with a claim of priority to Provisional Application Ser. No. 60/010,614. FIG. 15 shows how anastomosis channel 36 formed in any of the procedures described herein, can be dilated by a standard balloon 52 advanced over guide wire 51 for the purpose of ensuring that anastomosis channel 36 is wide enough to receive the flow. Further, this step may be necessary to properly dimension the anastomosis channel 36 prior to insertion of other devices such as the protrusive stent 41 seen in FIG. 13, or the non-protrusive stent 410 seen in FIG. 13a.

Figure 16:
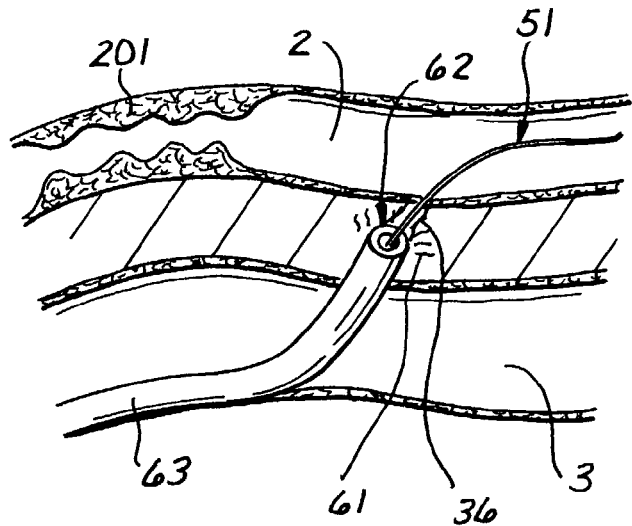
FIG. 16 is a longitudinal sectional showing of two adjacent blood vessels having an initial puncture tract or channel formed therebetween in accordance with the present invention, and further showing an energy emitting vaporization catheter being advanced over a guide wire which has been passed through the initially created puncture tract or channel, such vaporizing catheter being operable to form a finished blood passageway or an anastomosis channel having the desired dimensions.

In some cases, a stent may not be necessary to maintain the size of anastomosis channel 36 if enough material can be removed or ablated between coronary artery 2 and cardiac vein 3. In FIG. 16, a vaporization catheter 63 is shown being advanced over guide wire 51. Here, energy 61 is delivered to the anastomosis channel 36 through the distal portion 62 of the vaporization catheter 63 to create a properly dimensioned connection between artery and vein. Those skilled in the art will recognize that this vaporization catheter 63 may also be used to deliver thermal, cutting, welding or coagulative energy via several means including but not limited to laser, bipolar or monopolar radio frequency (RF), microwave, ultrasound, hot wire, or radiation. This vaporization catheter 63, as well as other devices useable to enlarge, modify or debulk an initially formed puncture tract or other channel, are fully described and claimed in copending U.S. patent application Ser. Nos. 08/730,327 and 08/730,496 which were filed on Oct. 11, 1996.

Figure 13:
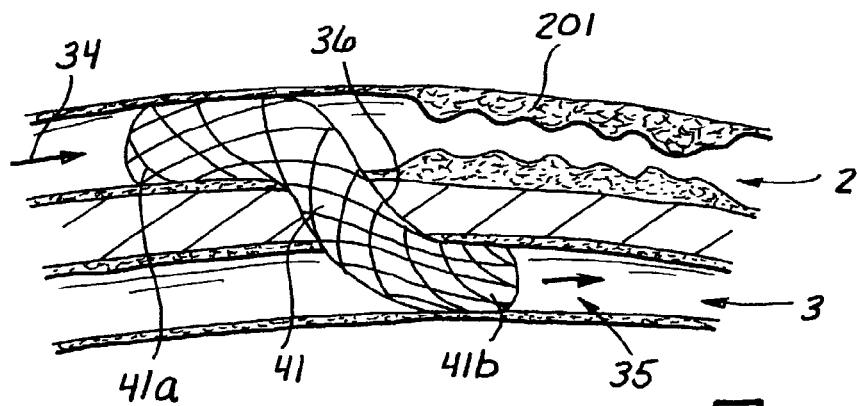
FIG. 13 is a longitudinal sectional view of adjacent blood vessels having a blood flow passageway or anastomosis channel formed therebetween in accordance with the present invention, and having a protrusive stent disposed within the passageway or channel and extending into the lumens of the blood vessels, such protrusive stent being optionally formed, wholly or in part, of a relatively dense material which will block the natural flow of blood through the lumen of at least one of the blood vessels.
Figure 14:
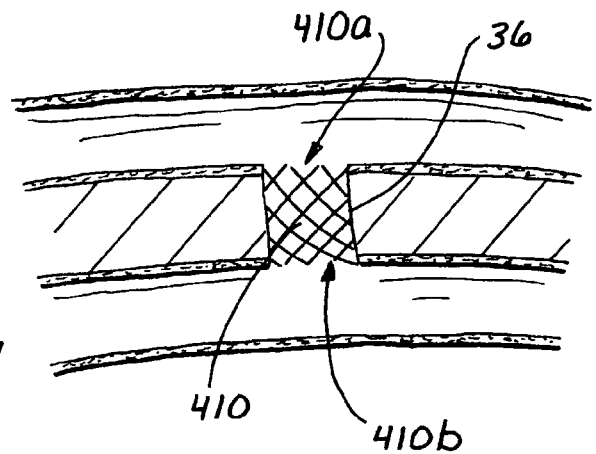
FIG. 14 is a longitudinal perspective view of adjacent blood vessels having a blood flow passageway (i.e., an anastomosis channel) formed therebetween and having a non-protrusive stent mounted within the blood flow passageway (i.e., an anastomosis channel) to maintain the dimensions of the blood flow passageway (i.e., an anastomosis channel).

In cases wherein stenting of the channel is necessary or desirable to maintain its desired dimensions, stents such as those shown in FIGS. 13 and 14 may be placed in the anastomosis channel 36 to control its dimensions, e.g. to prevent the channel 36 from expanding under pressure, constricting due to contraction of the surrounding tissue, or closing as a result of restenosis.

Figure 18:
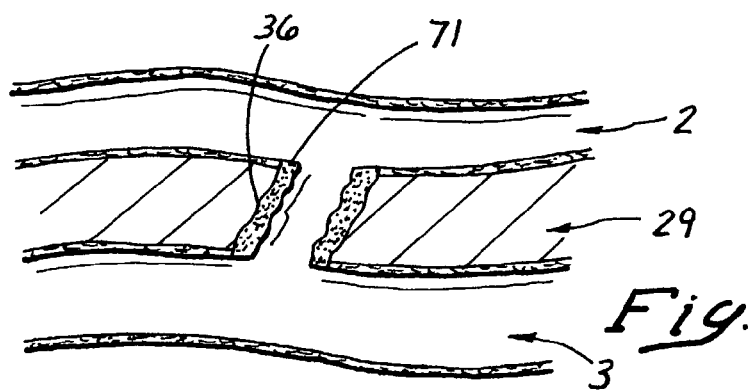
FIG. 18 is a longitudinal sectional view of adjacent blood vessels having a blood flow passageway or an anastomosis channel formed therebetween in accordance with the present invention, and having a polymer stent covering the walls of the passageway or an anastomosis channel.

Another method of maintaining the dimensions of anastomosis channel 36 permanently or temporarily during the healing and remodeling process is shown in FIG. 18. Here a polymer stent 71 is shown covering the walls of anastomosis channel 36. Such a polymer stent 71 may be placed either by insertion and dilation using a balloon catheter, or may be created in-situ using various methods known in the art and practiced by a company by the name of FOCAL (TM) located in Massachusetts. Such a polymer stent 71 may permit the temporary protection from the effects of restenosis or pseudoaneurysm formation, and may dissolve after a period of time to reduce the likelihood of any long lasting tissue reaction effects.

In some cases, the creation of an anastomosis channel may be undesirable, due to the high likelihood that problems such as restenosis or pseudoaneurysm will occur. However, the potential for such problems may be minimized or overcome by employing channel connecting methods and such as those shown in FIGS. 17, 19, 19a, 19b, 19c, 20 and 20a. These and other channel connection or clipping devices are more fully described and claimed in U.S. patent application Ser. Nos. 08/730,327 and 08/730,496 which were previously filed on Oct. 11, 1996, as well as in PCT International Patent Application No. PCT/US97/01463 entitled METHODS AND APPARATUS FOR ANASTOMOSIS OF ANATOMICAL CONDUITS, filed contemporaneously with this application and claiming priority to Provisional Application Ser. No. 60/010,614.

Figure 17:
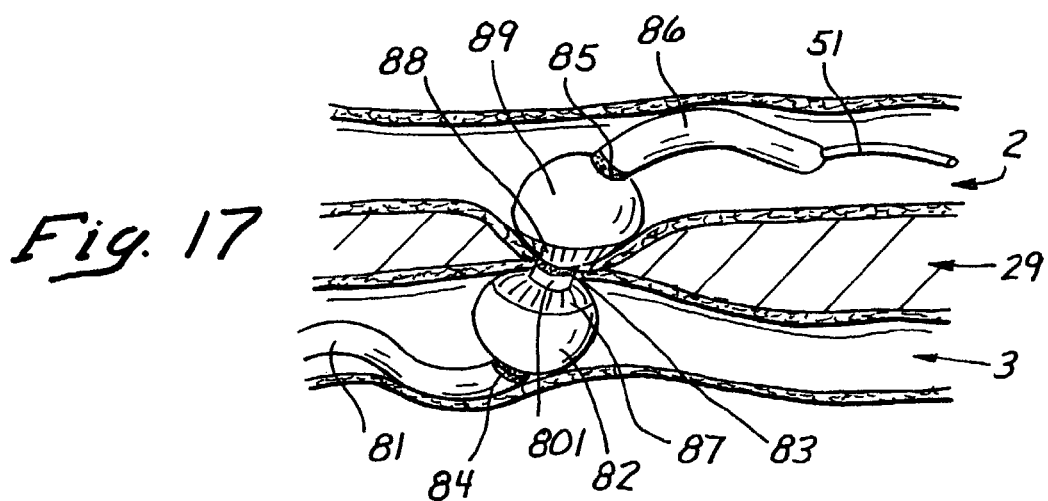
FIG. 17 is a longitudinal sectional showing of an adjacent blood vessels having a blood flow passageway or anastomosis channel formed therebetween in accordance with the present invention, and wherein a welding catheter system of the present invention is used to weld or fuse the tissue which surrounds the blood flow passageway or anastomosis channel, thereby establishing a firm connection between the openings formed in the adjacently situated blood vessels.

In FIG. 17, a welding catheter system is used to establish a firm connection between openings formed in adjacently situated vessels. This welding catheter system consists of a proximal welding catheter 81 and a distal welding catheter 86. After an anastomosis channel has been created through interstitial space 29 which exists between cardiac vein 3 and coronary artery 2, a guide wire 51 is inserted through the channel. Distal welding catheter 85 is then advanced over guide wire 51 and distal approximation balloon 89 is inflated. Subsequently, proximal welding catheter 81 may be advanced over the distal welding catheter 86. At that point, proximal approximation balloon 82 may be inflated, and the two balloons may be pulled into a position, opposing edges of the opening in the coronary artery 2 and cardiac vein 3. The approximation balloons and welding catheters may be equipped with one or more of the following components: intraweld electrodes 83, contralateral welding surfaces 87 and 88, and return electrodes 85 and 84 and a thermocouple 801. In this configuration, bipolar RF energy may be used to weld the two vessel openings together without the need for additional mechanical attachment devices. Energy will be delivered either between the contralateral welding surfaces 87 and 88 or between the intraweld electrodes 83 and the return electrodes 85 and 84. In either case, the temperature of the local tissue in and around the approximated two openings is elevated to a desired temperature measured by thermocouple 801. This temperature is maintained for a certain amount of time during which time the tissue is fused. After fusion, the power is turned off, the balloons are deflated, and the apparatus is removed, leaving the two openings fused around their perimeter.

Figure 19:
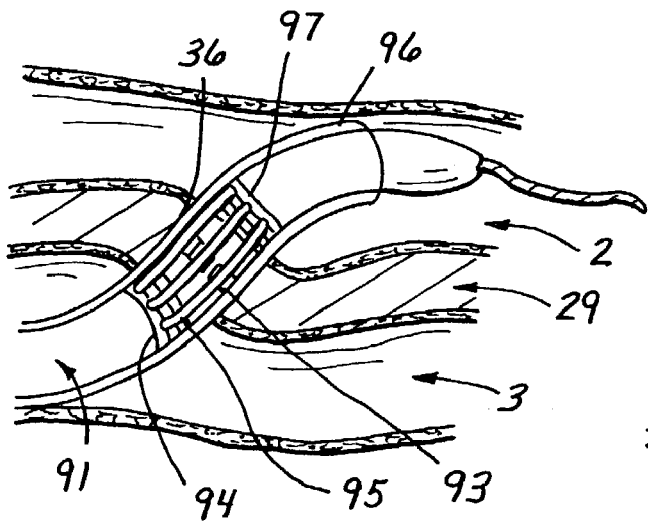
FIG. 19 is a longitudinal sectional showing of adjacent blood vessels having a blood flow passageway or anastomosis channel formed therebetween, and having a stapling catheter of the present invention positioned within such passageway or channel to install staples to connect the blood vessels and hold the passageway or channel in the desired alignment.
Figure 19A:
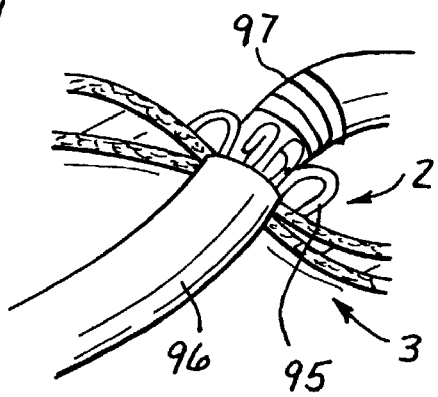
FIGS. 19a-19c show, in step-wise fashion, the manner in which the stapling catheter of FIG. 19 is utilized to install the staples within the blood flow passageway or anastomosis channel.
Figure 19B:
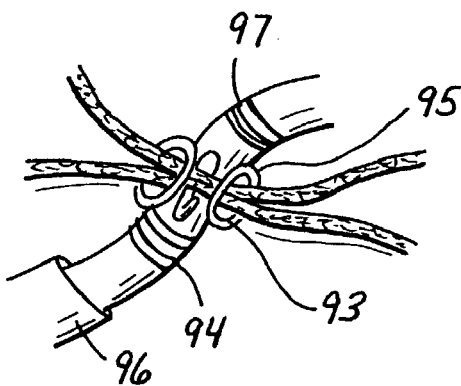
Figure 19C:
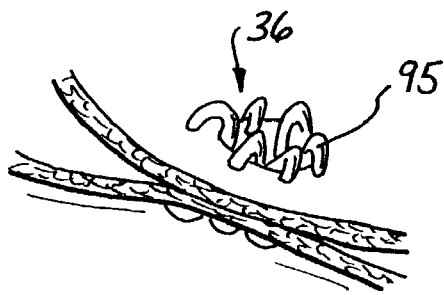

In FIG. 19 a mechanical stapling method is described to attach the two vascular openings. Stapling catheter 91 has outer sheath 96, optional heating coils 94 and 97, staples 95, and micromachine staple holders 93. Stapling catheter 91 is advanced through anastomosis channel 36 until the device is well into the coronary artery 2. The outer diameter of the outer sheath 96 is sized to slightly dilate the anastomosis channel 36 between the two vessels. Outer sheath 96 is pulled back until the full upper halves of staples 95 are exposed. This point of pull back is controlled at the proximal end of the catheter. The staples 95 are composed of either a spring like material such as stainless steel, or super elastic alloy such that they spring into a curved position as seen in FIG. 19a. This effect may also be accomplished using shape memory materials such as nitinol and adding heat through coil 97. Once staples' 95 upper halves have achieved their curved state, the stapling catheter 91 can be withdrawn, as shown in FIG. 18b, allowing the tips of the staples 95 to seat into the circumference of the opening in the coronary artery 2. Now the outer sheath 96 can be fully withdrawn (as shown in FIG. 19b), permitting the lower halves of the staples 95 to seat into the inner aspect of the circumference around the opening of the cardiac vein. Again this effect can be created either passively upon release of the sheath, or actively using heat from heating coil 94. While the passive approach is more simplified, the active approach allows for the reversal of the device using an injection of cold saline. This may be desirable in cases where the seating of the staples 95 was not accomplished correctly. Finally, once the staples' placement is assured, they may be released by the micromachine staple holders 93 resulting in the configuration shown in FIG. 18c, wherein staples 95 cause the tissue 36 to be maintained in an open condition. Those skilled in the art will recognize that other than utilizing micromachines, there may be several methods of staple release, including thermal material methods such as solder melting, thermal degradation of a retaining polymer or biomaterial, as well as mechanical methods such as the removal of a retaining wire, balloon expansion of a weak retaining material, or an unlocking motion of the stapling catheter 91 with respect to the staples 95 that could only be accomplished after the staples have been fixed in place. Devices similar to this stapling catheter 91 and staples 95 are described, claimed, and shown in FIGS. 9f-9f''' copending U.S. patent application Ser. No. 08/730,327 filed on Oct. 11, 1996.

Figure 20:
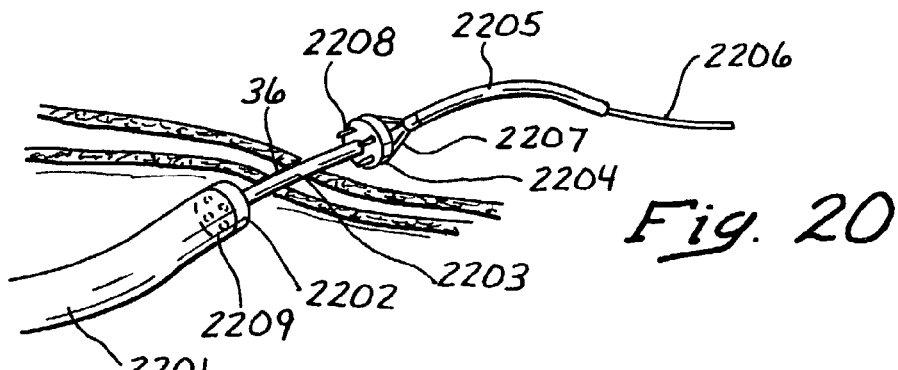
FIG. 20 is a longitudinal sectional view to adjacent blood vessels having a blood flow passageway or anastomosis channel formed therebetween, and having a clip-installing catheter device of the present invention passed through the passageway or anastomosis channel to install a clip therewithin.
Figure 20A:
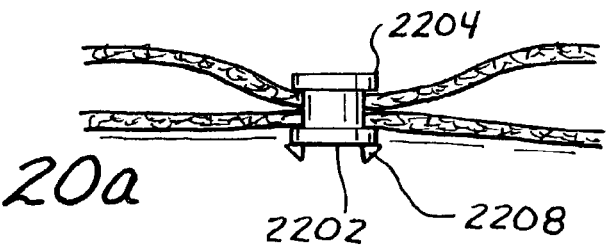
FIG. 20a is a longitudinal section view of the blood vessels shown in FIG. 20, having a clip of the present invention installed within the blood flow passageway or anastomosis channel formed between the blood vessels.

FIGS. 20-20a show another embodiment of an apparatus for holding together the openings formed in adjacent vessels. This embodiment utilizes a distal guide catheter 2205 which is inserted over a guide wire 2206. An upper clip 2204 is held to the distal guide catheter 2205 by a collapsible retaining unit 2207 located near the upper clip 2204. This assembly is advanced through anastomosis channel 36 until it is completely through. In this case, the collapsible retaining unit 2207 helps to dilate the anastomosis channel 36 since the upper clip 2204 is dimensioned to be slightly larger than the diameter of anastomosis channel 36. A proximal guide catheter 2201 with a lower clip 2202 at its tip are advanced over the distal guide catheter 2201 towards anastomosis channel 36. The two clips 2204 and 2202 are then pulled toward each other until tines 2208 of upper clip 2204 penetrate and lock into the receiving holes 2209 located in the lower clip 2202. Upon successful locking, the collapsible retaining unit 2207 is collapsed and both proximal and distal catheters are withdrawn leaving the clips behind as seen in FIG. 22a. The collapsible retaining unit may, for example, be a balloon, struts composed of shape memory material, or wire pins controlled at the proximal end of the catheter. A channel connection apparatus similar to that shown in FIGS. 20-20a is fully described claimed and shown in FIGS. 9a-9a' of copendining application Ser. No. 08/730,327 filed on Oct. 11, 1996, and such device is claimed in that application.

Figure 21:
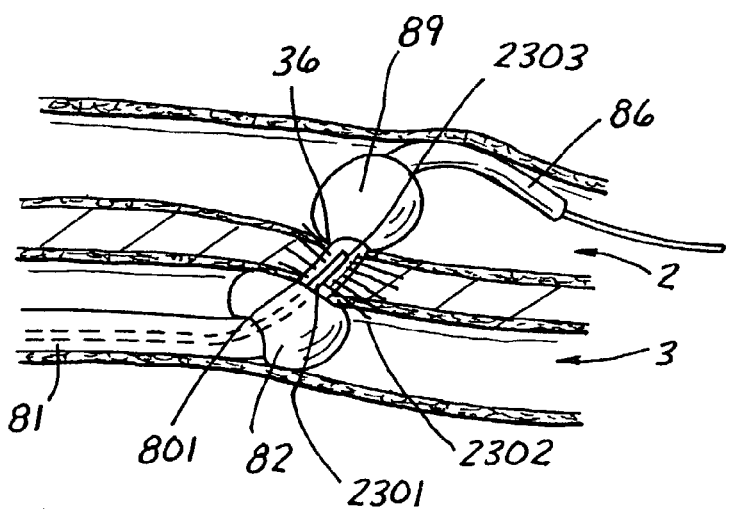
FIG. 21 is a longitudinal sectional showing of adjacent blood vessels having a blood flow passageway or anastomosis channel of the present invention formed therebetween, and an alternative embodiment of a welding catheter device passed through such passageway or channel to fuse or weld or tissue surrounding the channel.

Another welding device in accordance with an embodiment of the present invention is detailed in FIG. 21. Here a very similar scheme to that found in FIG. 17 is employed with the exception that energy is released from a central emitter core 2301 into the opposed openings of vessels 2 and 3. In this case, after the two openings are opposed, by balloons 89 and 81, a central emitter core is advanced into the center of the catheter assembly 81 and 86 to a position directly at the midpoint of anastomosis channel 36. Energy is emitted by this central emitter core to produce enough temperature in the local tissues surrounding the device to permit fusion. This energy and the emitter may be of the form of a 360 degree laterally firing laser fiber, microwave or other electromagnetic antennae, or locally mounted ultrasound producing piezoelectric crystal or laser emitter. Thermocouple 801 may also be helpful to define and control the welding process.

Figure 22:
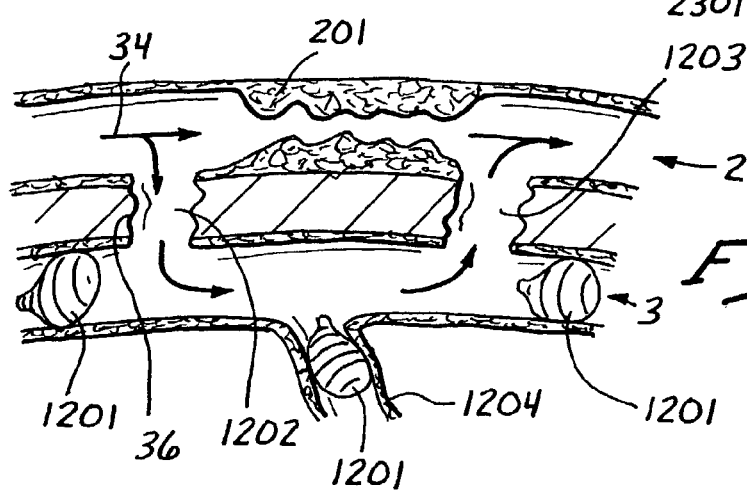
FIG. 22 is a longitudinal sectional showing of an adjacent coronary artery and coronary vein, wherein an in-situ coronary bypass procedure of the present invention has been completed.

FIG. 22 depicts the final result after the coronary bypass procedure is complete. Normal coronary flow 34 is bypassed around stenosis 201 through anastomosis channel 1202 into cardiac vein 3 and back into coronary artery 2 through anastomosis channel 1203. Here a generic embolization device 1201 is shown blocking the upstream and downstream cardiac vein 3 in addition to a tributary vein 1204. In the case where simply cardiac venous arterialization is desired, only the proximal embolization and attachment would be required.

FIGS. 23a and 23b depict a generalized TVIS access port 1301. The TVIS port has a housing 130 and an entry port 138 which permits the introduction of various instruments. The entry port 138 may also have the ability to maintain pressure or hemostasis within the catheter alone or when instruments are inserted through it. Catheter 133 has a proximal portion which forms the housing 130 and a distal portion which forms the tip 1302. The TVIS access port 1301 may also be provided with an imageable marker 139 and a stabilizing balloon 134 located at its distal portion. After the TVIS guide catheter 5 shown in FIG. 5 obtains interstitial access and leaves behind a guide wire, the distal tip of the TVIS access port 1301 is placed percutaneously over the guide wire and advanced to the interstitial location 138. Upon identification of the marker 139 outside the vessel 132, the balloon 134 is inflated. Those skilled in the art should recognize that stabilization means at the tip may also include locking wires, expandable cages, and expandable stent like frames. Once the TVIS access port is fixed in location, numerous other devices may be inserted for effecting a medical or therapeutic intervention. These include endoscopes 135, surgical tools 136 such as needles, cannula, catheter scissors, graspers, or biopsy devices, and energy delivery devices 137 such as laser fibers, bipolar and monopolar RF wires, microwave antennae, radiation delivery devices, and thermal delivery devices. Once one or more TVIS access ports 1301 are placed, various surgical procedures may be conducted completely through the vascular system on tissues in the periphery.

FIG. 24 shows another embodiment of a TVIS guide catheter 146 in accordance with the present invention. Here the TVIS guide catheter 146 is shown having an actively deflectable distal tip 145. In this case, the distal tip 145 is deflected by a shape memory material 142 embedded in the distal tip 145 of the device. When this material is heated by heating coil 147, the material rapidly bends into a desired configuration. A working channel 143 is provided for the advancement of the desired TVIS device. Here a needle 141 is shown infusing a drug 140 into the perivascular tissue. As discussed previously, the TVIS guide catheter 146 may also include a balloon 144 for stabilization within the vessel, and a passive imaging marker 148.

FIG. 23 depicts the same TVIS catheter 146 with the additional component of an active imaging device 23 as described previously. Also in FIG. 25, the TVIS probe 27 and TVIS sheath 26 are shown exiting the working channel 143 at the distal tip 145. Further, a flush channel 150 is also shown.

Figure 26:
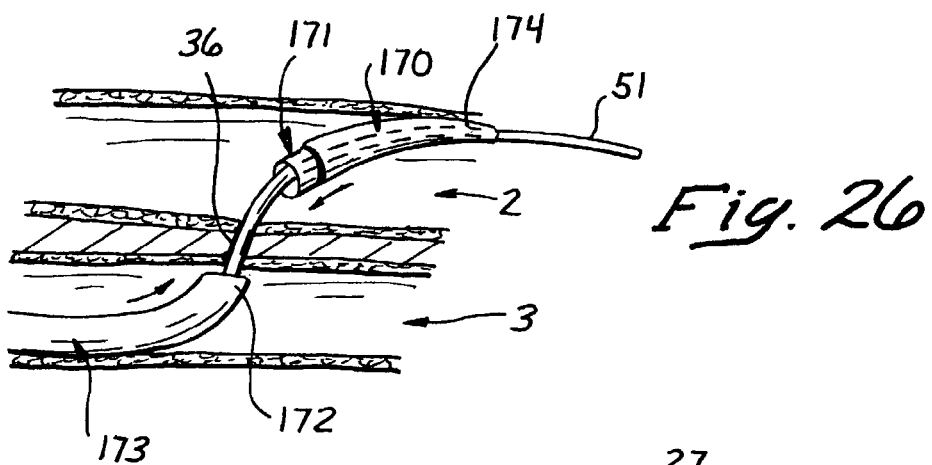
FIG. 26 is a longitudinal section showing of adjacent blood vessels having an initial puncture tract formed therebetween and a catheter borne retrograde tissue cutting assembly of the present invention positioned therewithin to enlarge the initial puncture tract to form the desired anastomosis channel or blood flow passageway.

FIG. 26 depicts another method of creating an accurately sized anastomosis channel 36 in accordance with an embodiment of the present invention. A retrograde tissue cutter catheter assembly 173 is advanced over guide wire 51 through anastomosis channel 36. The retrograde tissue cutter assembly 173 has a cylindrical blade 171 attached to a dilating tip 170. The tip 170 is advanced through the anastomosis channel 36 until the blade 171 is beyond the opening within the artery 2. Once that position is found, a much larger base catheter 172 id advanced against the proximal opening within vein 3. The blade 171 and tip 170 are then pulled back against the edges of anastomosis channel 36, capturing tissue within the cylindrical blade 171 as it is pressed against the base catheter 172. After the assembly 173 is removed, the resulting anastomosis channel 36 is the size of the outer diameter of the cylindrical blade 171. A similar retrograde tissue cutter assembly is described, claimed and shown in FIG. 8f of U.S. patent application Ser. No. 08/730,327 filed on Oct. 11, 1996.

Figure 27:
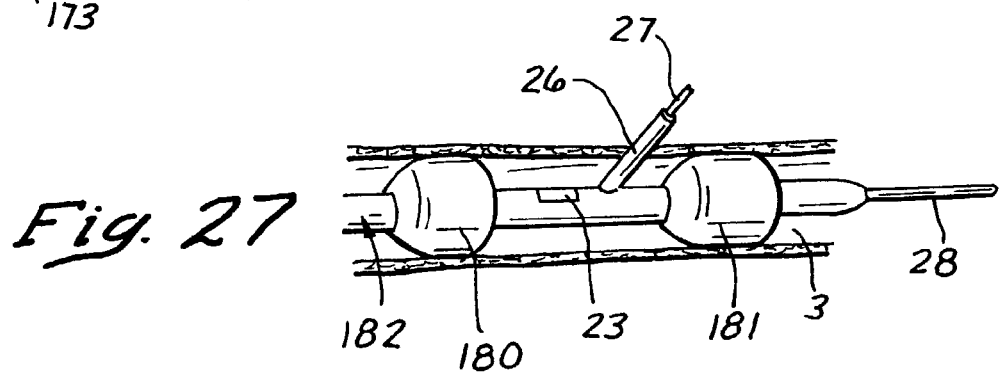
FIG. 27 is a longitudinal sectional showing of a blood vessel having another embodiment of a TVIS guide catheter incorporating proximal and distal isolation balloons.

FIG. 27 depicts a TVIS guide catheter 182 in accordance with an embodiment of the present invention where a distal balloon 181 and a proximal balloon 180 isolate a section of the artery which is to be penetrated. This may be useful when using the TVIS guide catheter 182 in a high pressure vessel such as an artery. Such a catheter 182 may be used in a manner generally similar to the catheter 5 in FIG. 2.

Figure 28A:
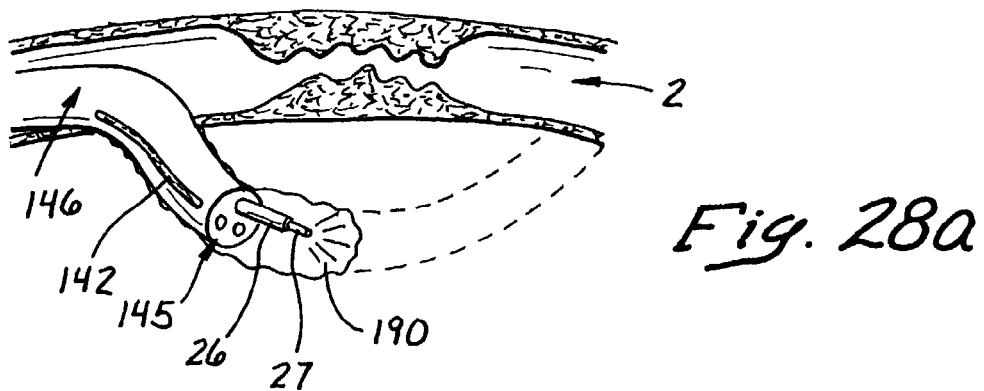
FIG. 28a is a longitudinal sectional showing of an obstructed artery and an adjacent area of tissue, with a TVIS guide catheter and TVIS device of the present invention being advanced through the adjacent tissue to form an interstitial tunnel or blood flow passageway around the obstruction.
Figure 28B:
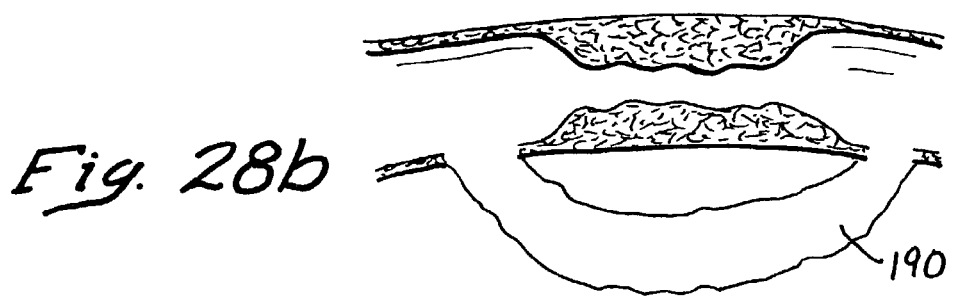
FIG. 28b is a longitudinal sectional showing of the blood vessel of FIG. 28a, following formation of the interstitial tunnel around the obstruction.

Another alternative method in accordance with an embodiment of the present invention for bypassing a section of a vessel is depicted in FIGS. 28a and 28b. FIG. 28a depicts a TVIS guide catheter 146, such as described in FIGS. 14 and 15, but here having a distal tip 145 with an actively controlled shape memory material 142. Here the TVIS guide catheter 146 itself is shown tunneling through surrounding tissue utilizing probe 27 and sheath 26 to guide the way. Ultimately, the catheter 145 creates a tunnel 190 which can be used to allow flow from one point to another point in artery 2 as shown in FIG. 28b.

Figure 29A:
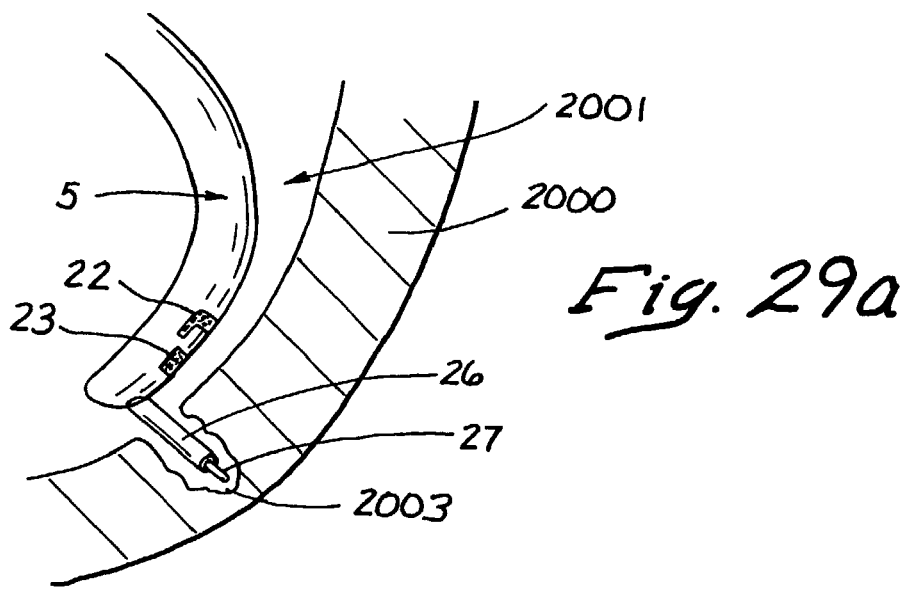
FIG. 29a is a sectional showing of a coronary blood vessel and an adjacent segment of myocardium, wherein a TVIS catheter or probe of the present invention have been advanced into the coronary blood vessel and is being used to form an interstitial channel in the myocardium to enhance perfusion of that region of the myocardium.
Figure 29B:
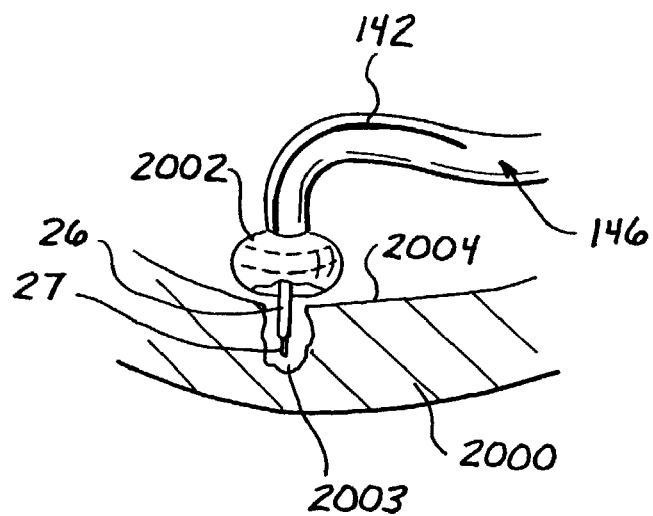
FIG. 29b is a sectional showing of a coronary blood vessel and an adjacent segment of myocardium, wherein an alternative TVIS catheter or probe of the present invention have been advanced into the coronary blood vessel and is being used to form an interstitial channel in the myocardium to enhance perfusion of that region of the myocardium.
Figure 29C:
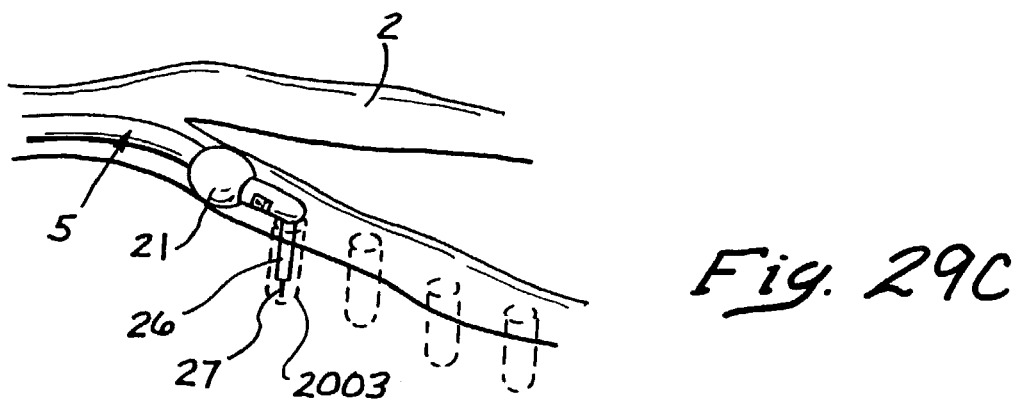
FIG. 29c is a sectional showing of a bifurcated coronary blood vessel wherein a TVIS catheter of the present invention has been positioned, such TVIS catheter being utilized to form a series of interstitial channels to enhance perfusion of that region of the myocardium.

FIGS. 29a-29d depict the use of a passageway-forming catheter device for transmyocardial revascularizations in accordance with an embodiment of the present invention. FIG. 29a shows how the TVIS guide catheter 5 can be placed within the ventricle 2001 of the heart. The TVIS probe 27 is shown here creating an elongate channel 2003 through the heart muscle 2000. This channel may result in a direct communication between the ventricle and the small capillary vascular bed within the heart muscle 2000. FIG. 29b depicts how the alternative TVIS guide catheter 146 of FIG. 27a may be used to create these elongate channels 2003 within the heart. The TVIS guide catheter 145 is further modified in this case with a balloon tip 2002 for the purpose of covering the channel 2003 during vaporization; the balloon 2002 may be additionally assisted in assuring seating against the ventricle wall 2004 by providing a suction through the catheter 146 to an opening at the distal end of balloon 2002. Finally, FIG. 29c depicts TVIS guide catheter 5 creating several channels 2003 transvascularly, permitting blood flow from the vessel directly into the heart. Guide catheter 5 may use RF, electrical or mechanical energy to create a hole.

Figure 29D:
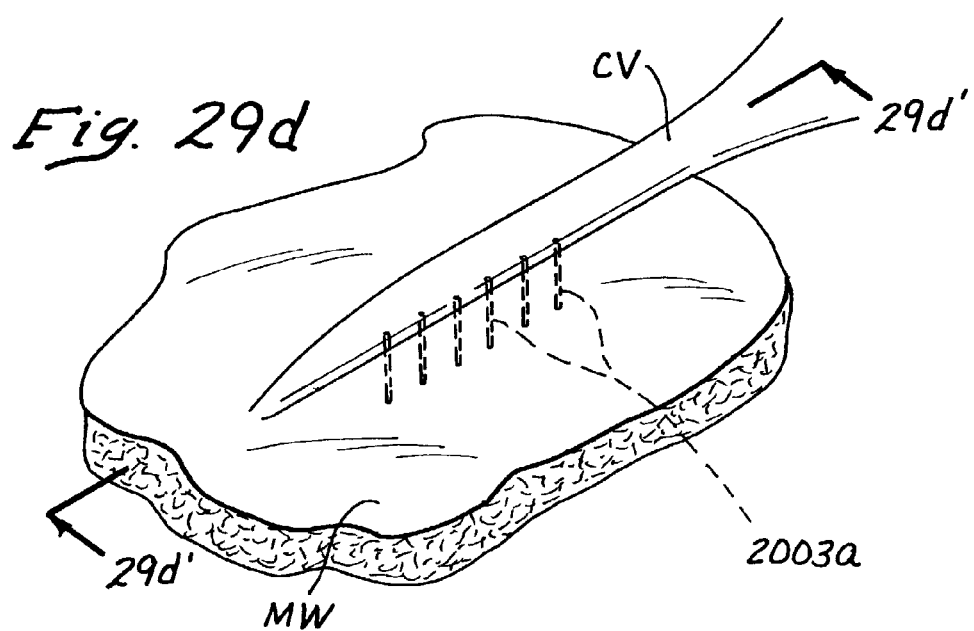
FIG. 29d is sectional showing of a coronary vein and an adjacent segment of myocardium which forms a wall of the left ventricle of the heart, and a series of transmyocardial blood flow passageways having been formed between the coronary vein and the left ventricle in accordance with the present invention, and the coronary vein remaining unobstructed and unlighted such that oxygenated blood may flow from the left ventricle, through the transmyocardial channels, through the coronary vein and into the coronary sinus thereby providing for continual enhanced perfusion of that region of the myocardium.
Figure 29D:
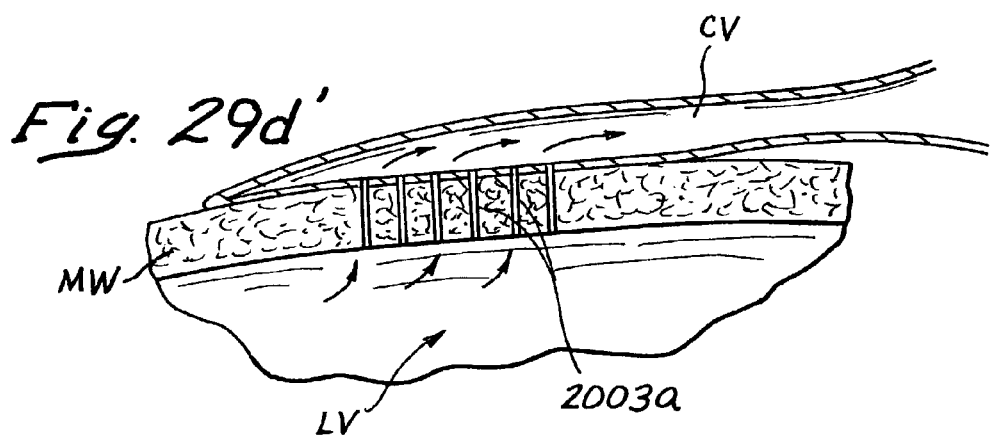

FIGS. 29d and 29d' show an alternative transmyocardial revascularization procedure wherein one of the TVIS guide catheters 5, 145 and the associated TVIS probe 27 have been advanced into a coronary vein CV and utilized to form a series of transmyocardial channels 2003a which extend from the lumen of the coronary vein CV, through the myocardial wall MW into the underlying left ventricle LV of the heart. Following removal of the guide catheter 5 or 146 and probe 27, the coronary vein CV remains open and unobstructed such that oxygenated blood may flow from the left ventricle LV, through the transmyocardial channels 2003a, into the lumen of the coronary vein CV, and through the coronary vein CV into the coronary sinus. In this manner, substantially continuous flow of oxygenated blood will be permitted to pass from the left ventricle LV, through the transmyocardial channels 2003a, and through the coronary vein CV, thereby providing for substantially continual perfusion of the region of myocardium adjacent those channels 2003a.

Figure 30:
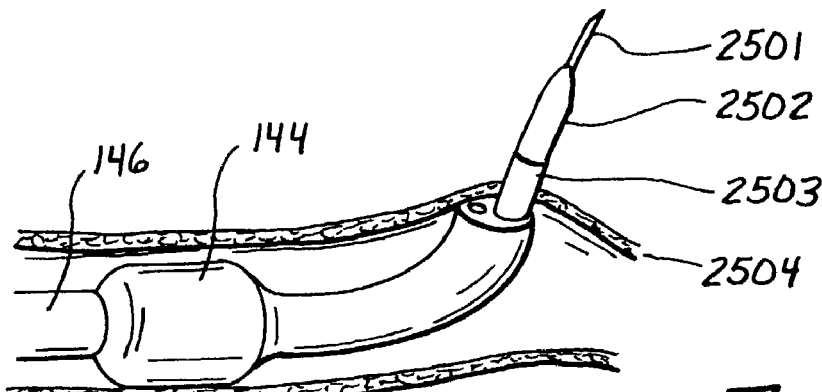
FIG. 30 is a longitudinal section showing of a blood vessel having a TVIS catheter and ancillary devices positioned therewith in accordance with the present invention.

FIG. 30 depicts more detail of the various types of devices which may be advanced through the TVIS catheter 146 in accordance with an embodiment of the present invention. Here, a wire 2501 is shown having advanced over it a dilator 2502 and a sheath 2503 through the vessel wall 2504.

Figure 31A:
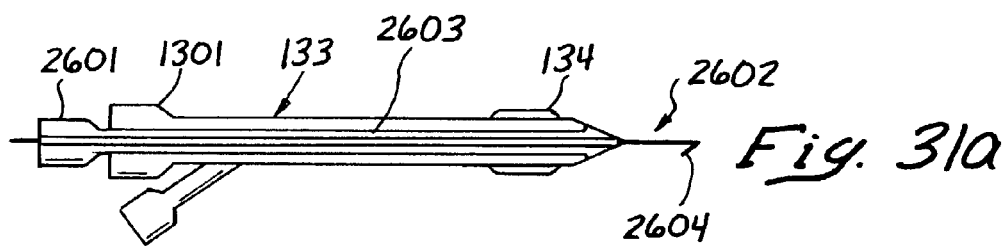
FIG. 31a is a longitudinal sectional view of a portion of TVIS catheter of the present invention having a locking guide wire passed therethrough.
Figure 31B:

Alternatively, as shown in FIGS. 31a and 31b, a separate sheath such as the one shown in FIG. 13 can be advanced. Initially, the TVIs catheter is used to place a locking guide wire 2602 into the tissue. The guide wire has a very small locking tie 2604 which serves to anchor it in the tissue during device exchange. Then, over the locking guide wire 2602 the TVIS port introducer assembly shown in FIG. 30a is advanced. The assembly includes a dilator 2601 within a catheter 133. The catheter 133 is provided with a stabilization means 134 illustrated here as a balloon. After the catheter 133 is in place, and the stabilization means 134 is deployed, the dilator 2601 and the locking guide wire 2602 are removed. Depending on the situation, housing 1301 may or may not be equipped with a valve to prevent backflow into the catheter 133. Subsequently, various instruments may be inserted into the catheter 133 as described previously.

Figure 32A:
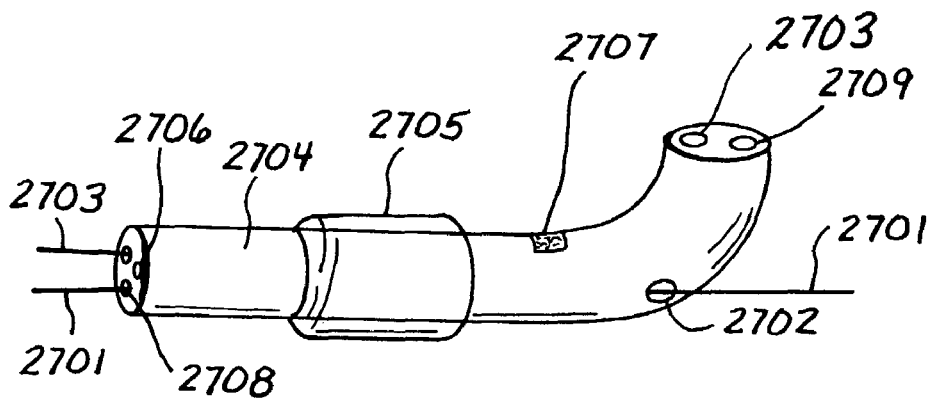
FIG. 32a is a perspective showing of a portion of a TVIS catheter of the present invention having a deflectable or curvable distal portion.
Figure 32B:
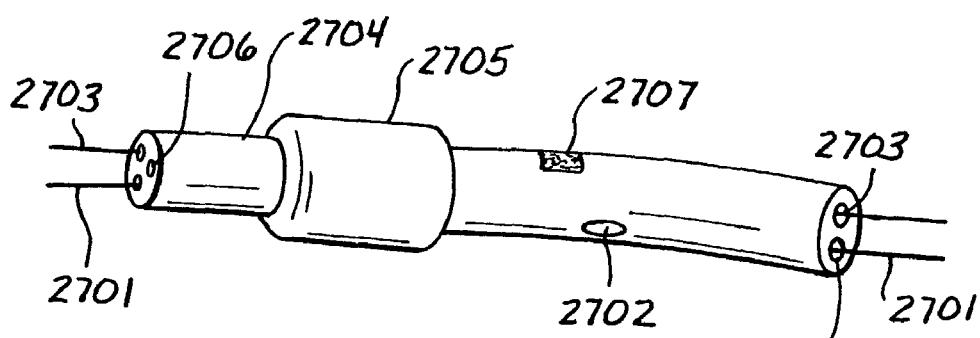
FIG. 32b is a plan view of the TVIS catheter of FIG. 32a in a non-curved, straight configuration.

Another embodiment of the TVIS catheter in accordance with the present invention can be seen as item 2704 in FIGS. 32a and 32b. Here the TVIs catheter 2704 is made with a pre-formed curve seen in FIG. 31a. When the catheter is constrained, as seen in FIG. 31b, it can be held in a linear position. Guide wire 2701 can be seen exiting the guide wire lumen 2709 when the catheter 2704 is held linearly (FIG. 32b) and can exit the side hole 2702 when the catheter is allowed to regain its pre-formed shape (FIG. 32a). A TVIS probe 2703 is shown entering another channel and exiting the device at the tip in either position. The catheter 2704 can be used in the manner of other catheters discussed previously but has the benefit of being able to cause the tip to be curved in a desired direction.

A further embodiment of a TVIS catheter 2800 in accordance with the present invention is shown in FIG. 33a. Here the two openings in the vessels are made with a vaporizing energy beam 2805 instead of a probe. This method utilizes an energy guide 2801, which beams energy at a deflecting plate 2802, which in turn sends the energy laterally into the tissue. The duration and energy level must be finely set to ensure that the opposite wall of vessel 2 is not damaged. Also shown in the diagram is the optional guide wire 2804, which may be used to block or signal the penetration of the laser energy.

FIG. 33b depicts another mechanism for widening or cutting the hole in accordance with an embodiment of the present invention. Here the device is advanced through the tissue channel over guide wire 3003, the cutting wings 3001 are expanded by moving sheath 3004 relative to central body 3002. The wings 3001 may be sharp, or the use of additional energy may be used to widen the hole as the device with withdrawn through the tissue channel.

A further embodiment of a TVIS catheter in accordance with the present invention is illustrated as item 2900 in FIGS. 34a and 34b. As shown therein, catheter 2900 includes a channel 2901 along its longitudinal axis and terminating in single distal opening 2902. A TVIS probe 2903 is disposed within the channel 2901 in a linear position. In a preferred embodiment, TVIS probe 2903, rather than the catheter itself (FIGS. 31a and 31b) is provided with a shape memory ability such that once it is moved from within channel 2901, TVIS probe 2903 is capable of resuming its pre-formed curve, as shown in FIG. 29b, to subsequently form, through a vessel, an opening that is less than 180 degrees relative to the longitudinal axis of the catheter 2900. A guide wire 2904 may also be movably disposed within the probe 2903. To this end, once probe 2903 has been moved from within channel 2901 through opening 2902 and has resumed its pre-formed shape, guide wire 2904 may be advanced within the probe 2903 to exit across the same opening 2902. To form a channel 2905, it is preferably that guide wire 2904 be withdrawn slightly into the probe 2903 so that the probe's distal portion 2908 is exposed for penetrating through vessel 2906 across to vessel 2907. Once probe 2903 is within vessel 2907, guide wire 2904 may be advanced from within the probe 2903 and into the lumen of vessel 2907. It should be appreciated that although provided with a pre-formed shape probe 2903, catheter 2900 nevertheless can be used in the manner of other catheters previously discussed.

What is claimed is:

1. A welding catheter system for establishing a fluid connection between adjacently situated first and second anatomical structures having walls and lumens, wherein an anastomosis channel extends from the lumen of the first anatomical structure, through its wall, through the wall of the second anatomical structure and into the lumen of the second anatomical structure, said system comprising:
   a proximal welding catheter member having a proximal approximation balloon having a deflated configuration, an inflated configuration and a first tissue-fusing member on a distal portion thereof;
   a distal welding catheter member having distal approximation balloon having a deflated configuration, an inflated configuration and a second tissue-fusing member on a proximal portion thereof; and
   a guidewire;
   the guidewire being advanceable from the first anatomical structure, through the anastomosis channel and into the second anatomical structure;
   the proximal and distal welding catheter members being advanceable over the guidewire with the proximal and distal approximation balloons in deflated configurations, to positions where the proximal approximation balloon is in the first anatomical structure and the distal approximation balloon is in the second anatomical structure, the proximal and distal approximation balloons being thereafter inflatable to inflated configurations and positionable so that the tissue-fusing members on the proximal and distal portions of the approximation balloons abut against the walls of the first and second anatomical structures adjacent to the anastomosis channel;
   the first and second tissue-fusing members located on the proximal and distal portions of the approximation balloons being thereby operable to cause portions of the walls of the first and second anatomical structures located adjacent to the anastomosis channel and between the proximal and distal approximation balloons to become fused to each other.

2. The welding catheter system of claim 1 wherein said tissue-fusing members cause fusing of the tissue by emission of an energy type selected from the group of energy types consisting:
   heat;
   laser light;
   electrical current;
   radiofrequency energy; and
   ultrasound.

* * * * *